US009347092B2

(12) United States Patent
Roesler et al.

(10) Patent No.: US 9,347,092 B2
(45) Date of Patent: *May 24, 2016

(54) SOLID SUPPORT FOR HIGH-THROUGHPUT NUCLEIC ACID ANALYSIS

(75) Inventors: Angelika Roesler, Sindelsdorf (DE); Thomas Froehlich, Bichl (DE); Dieter Heindl, Paehl (DE)

(73) Assignee: ROCHE MOLECULAR SYSTEM, INC., Pleasanton, CA (US)

( * ) Notice: Subject to any disclaimer, the term of this patent is extended or adjusted under 35 U.S.C. 154(b) by 962 days.

This patent is subject to a terminal disclaimer.

(21) Appl. No.: 12/705,679

(22) Filed: Feb. 15, 2010

(65) Prior Publication Data

US 2010/0248991 A1    Sep. 30, 2010

(30) Foreign Application Priority Data

Feb. 25, 2009 (EP) ...................................... 09002628

(51) Int. Cl.
*C12Q 1/68*    (2006.01)
(52) U.S. Cl.
CPC .................................... *C12Q 1/6844* (2013.01)
(58) Field of Classification Search
None
See application file for complete search history.

(56) References Cited

U.S. PATENT DOCUMENTS

| | | | |
|---|---|---|---|
| 5,118,801 A | 6/1992 | Lizardi et al. | |
| 5,137,806 A | 8/1992 | LeMaistre et al. | |
| 5,258,506 A | 11/1993 | Urdea et al. | |
| 5,496,699 A | 3/1996 | Sorenson | |
| 5,521,301 A | 5/1996 | Wallace et al. | |
| 5,595,890 A | 1/1997 | Newton et al. | |
| 5,639,603 A | 6/1997 | Dower et al. | |
| 5,639,611 A | 6/1997 | Wallace et al. | |
| 5,641,658 A | 6/1997 | Adams et al. | |
| 5,677,152 A | 10/1997 | Birch et al. | |
| 5,693,502 A | 12/1997 | Gold et al. | |
| 5,773,258 A | 6/1998 | Birch et al. | |
| 5,792,607 A | 8/1998 | Backman et al. | |
| 5,804,375 A | 9/1998 | Gelfand et al. | |
| 5,871,908 A | 2/1999 | Henco et al. | |
| 6,090,592 A | 7/2000 | Adams et al. | |
| 6,174,670 B1 | 1/2001 | Wittwer et al. | |
| 6,210,891 B1 | 4/2001 | Nyren et al. | |
| 6,218,530 B1 * | 4/2001 | Rothschild et al. | 536/25.32 |
| 6,300,070 B1 * | 10/2001 | Boles et al. | 435/6.11 |

FOREIGN PATENT DOCUMENTS

| | | |
|---|---|---|
| DE | 19937234 C2 | 2/2001 |
| EP | 0744470 A1 | 11/1996 |
| EP | 0932700 B1 | 8/2001 |
| EP | 1275735 A1 | 1/2003 |
| KR | 10-2007-0044677 A | 4/2007 |
| WO | 92/02528 A1 | 2/1992 |
| WO | 96/37630 A1 | 11/1996 |
| WO | 99/41007 A3 | 8/1999 |
| WO | 00/50432 A3 | 8/2000 |
| WO | 01/12862 A3 | 2/2001 |
| WO | 01/62982 A3 | 8/2001 |
| WO | 02/14555 A3 | 2/2002 |
| WO | 2004/038038 A2 | 5/2004 |
| WO | 2004/069849 A3 | 8/2004 |
| WO | 2004/070007 A3 | 8/2004 |
| WO | 2005/003375 A3 | 1/2005 |
| WO | 2006/117556 A3 | 11/2006 |
| WO | 2007/081387 A1 | 7/2007 |
| WO | 2007/082713 A1 | 7/2007 |
| WO | 2007/111937 A1 | 10/2007 |
| WO | 2007/136736 A3 | 11/2007 |

OTHER PUBLICATIONS

Rehman et al (1999 Nucleic Acids Research 27: 649-55).*
European Search Report issued Jun. 4, 2010 in European Application No. 10001884.5.
Braeckmans, Kevin et al., Encoding Microcarriers: Present and Future Technologies, Nature Reviews, Jun. 2002, pp. 447-456, vol. 1.
Chitkul, Borden et al., A new bio-compatible pH cleavable linker for solid-phase synthesis of a squalamine analogue, Tehtrahedron Letters, 2001, pp. 6211-6214, vol. 42.
Dell'Aquila, Christelle et al., Photolabile Linker for the Solid-Phase Synthesis of Base-Sensitive Oligonucleotides, Tetrahedron Letters, 1997, pp. 5289-5292, vol. 38, No. 30.
Di Giusto, Daniel A. and King, Garry C., Special-Purpose Modifications and Immobilized Functional Nucleic Acids for Biomolecular Interactions, Topics in Current Chemistry, 2006, pp. 131-168, vol. 261.
Finkel, Nancy H. et al., Barcoding the Microworld, Analytical Chemistry, Oct. 1, 2004, pp. 352A-359A, vol. 76.
Hausch, Felix and Jaschke, Andres, Multifunctional DNA conjugates for the in vitro selection of new catalysts, Nucleic Acids Research, 2000, 3 pages, vol. 28, No. 8, e35.
Hausch, Felix and Jaschke, Andres, Multifunctional dinucleotide analogs for the generation of complex RNA conjugates, Tetrahedron, 2001, pp. 1261-1268, vol. 57.
Kainz, Peter et al., Specificity-Enhanced Hot-Start PCR: Addition of Double-Strangded DNA Fragments Adapted to the Annealing Temperature, BioTechniques, Feb. 2000, pp. 278-282, vol. 28, No. 2.
Keller, Keith A. et al., A thermally-cleavable linker for solid-phase synthesis, Tetrahedron Letters, 2005, pp. 1181-1184, vol. 46.
Kellogg, D. E. et al., TaqStart Antibody(TM): "Hot Start" PCR Facilitated by a Neutralizing Monoclonal Antibody Directed Against Taq DNA Polymerase, Biotechniques, 1994, pp. 1134-1137, vol. 16, No. 6.
Kokoris, Mark et al., High-throughput SNP Genotyping With the Masscode System, Molecular Diagnosis, 2000, pp. 329-340, vol. 5, No. 4.

(Continued)

*Primary Examiner* — Christopher M Gross
(74) *Attorney, Agent, or Firm* — Carol Johns; Olga Kay

(57) ABSTRACT

The present invention provides a solid support which is preferably a bead comprising at least two sequence specific amplification primers wherein at least one primer is bound to the support with an inducible cleavable linker. The present invention also provides various method for preparing a solid support comprising at least two sequence specific primers, further characterized in that at least one of the primers is cleavable.

4 Claims, 11 Drawing Sheets

(56) References Cited

OTHER PUBLICATIONS

Lin, Yun and Jayasena, Sumedha D., Inhibition of Multiple Thermostable DNA Polymerases by a Heterodimeric Aptamer, Journal of Molecular Biology, 1997, pp. 100-111, vol. 271.

Margulies, Marcel et al., Genome sequencing in microfabricated high-density picolitre reactors, Nature, Sep. 15, 2005, pp. 376-380, vol. 437.

Matthews, Jayne A. and Kricka, Larry J., Analytical Strategies for the Use of DNA Probes, Analytical Biochemistry, 1988, pp. 1-25, vol. 169.

Ng, Patrick et al., Multiplex sequencing of paired-end ditags (MS-PET): a strategy for the ultra-high-throughput analysis of transcriptomes and genomes, Nucleic Acids Research, 2006, 10 pages, vol. 34, No. 12, e84.

Olejnik, Jerzy et al., Photocleavable aminotag phosphoramidites for 5'-termini DNA/RNA labeling, Nucleic Acids Research, 1998, pp. 3572-3576, vol. 26, No. 15.

Ordoukhanian, Phillip and Taylor, John-Stephen, Design and Synthesis of a Versatile Photocleavable DNA Building Block. Application to Phototriggered Hybridization, Journal of the American Chemical Society, 1995, pp. 9570-9571, vol. 117, No. 37.

Piggott, Andrew M. and Karuso, Peter, Synthesis of a new hydrophilic o-nitrobenzyl photocleavable linker suitable for use in chemical proteomics, Tetrahedron Letters, 2005, pp. 8241-8244, vol. 46.

Saran, Dayal and Burke, Donald H., A Versatile Photocleavable Bifunctional Linker for Facile Synthesis of Substrate-DNA Conjugates for the Selection of Nucleic Acid Catalysts, Bioconjugate Chemistry, 2007, pp. 275-279, vol. 18, No. 1.

Steinberg, Gali et al., Strategies for Covalent Attachment of DNA to Beads, Biopolymers, 2004, pp. 597-605, vol. 73.

Steinberg-Tatman, Gali et al., Synthetic Modification of Silica Beads That Allows for Sequential Attachment of Two Different Oligonucleotides, Bioconjugate Chemistry, 2006, pp. 841-848, vol. 17, No. 3.

Sun, Lan et al., Surface-Enhanced Raman Scattering Based Nonfluorescent Probe for Multiplex DNA Detection, Analytical Chemistry, Jun. 1, 2007, pp. 3981-3988, vol. 79, No. 11.

Tong, Anthony K. et al., Combinatorial fluorescence energy transfer tags for multiplex biological assays, Nature Biotechnology, Aug. 2001, pp. 756-759, vol. 19.

Wenzel, T. et al., Genosnip: SNP Genotyping by MALDI-TOF MS using Photocleavable Oligonucleotides, Nucleosides, Nucleotides & Nucleic Acids, 2003, pp. 1579-1581, vol. 22, Nos. 5-8.

Wittebolle, Lieven et al., Optimisation of the amino-carboxy coupling of oligonucleotides to beads used in liquid arrays, 2005, Journal of Chemical Technology and Biotechnology, 2006, pp. 476-480, vol. 81.

Xu, Xiaoyang et al., Asymmetric Functionalization of Gold Nanoparticles with Oligonucleotides, Journal of the American Chemical Society, 2006, pp. 9286-9287, vol. 128, No. 29.

Zatsepin, Timofei S. et al., Use of Carbonyl Group Addition-Elimination Reactions for Synthesis of Nucleic Acid Conjugates, Bioconjugate Chemistry, 2005, pp. 471-489, vol. 16, No. 3.

* cited by examiner

SOLID SUPPORT FOR HIGH-THROUGHPUT NUCLEIC ACID ANALYSIS

SEQUENCE LISTING

The instant application contains a Sequence Listing which has been submitted via EFS-Web and is hereby incorporated by reference in its entirety. Said ASCII copy, created on Jan. 15, 2010, is named 25935US.txt and is 2,880 bytes in size.

RELATED APPLICATIONS

This application claims priority to European patent application EP 09002628.7 filed Feb. 25, 2009.

FIELD OF THE INVENTION

This invention relates to the area of nucleic acid analysis and in particular the miniaturized, highly parallel detection of nucleic acid sequences and analysis of differences in nucleic acid sequences.

The invention is based on the idea of providing a solid support to which sequence specific primers are bound, with one being cleavable and the other being non-cleavable, in order to analyze specific sequences or detect the presence of a SNP, a mutation or any particular DNA or RNA species of interest.

BACKGROUND OF THE INVENTION

Recently, an ultra-high throughput sequencing system based on pyrophosphate sequencing was disclosed which allows for the sequencing of a bacterial genome in essentially not more than one week (WO 04/70007, WO 05/03375, Margulies, M., et al., Nature 437 (2005) 376-80). Starting from sheared genomic DNA, single molecule fragments are bound to beads which are captured in a PCR-reaction-mixture-in-oil emulsion. Amplification then results in a library of clonally amplified DNA with each bead carrying multiple copies of the same fragment.

After breakage of the emulsion and denaturation of the PCR products into single strands, beads are deposited into the multiple wells of a fiber-optic picotiter plate such that one well carries not more than a single bead. Subsequently, in a sequencing by synthesis reaction, a primer extension reaction is performed, where the 4 different A, G, C, and T nucleoside triphosphates or their respective analogs are supplied in a repetitive series of events and the sequence of the nascent strand is inferred from chemical products derived from the extension reaction catalyzed by the DNA polymerase. In particular, the sequencing by synthesis reaction is a pyrophosphate sequencing reaction, characterized in that generation of pyrophosphate is detected as follows:

PPi+adenosine 5' phosphosulfate (APS)→ATP, catalyzed in the presence of Apyrase
ATP+luciferin→light+oxy luciferin, catalyzed in the presence of Luciferase
Detection of luminescence of oxyluciferin With the ultra high throughput sequencing system as disclosed in WO 04/70007 and WO 05/03375, more than 1 000 000 pyrophosphate sequencing reactions can be carried out simultaneously. The generation of Pyrophosphate is triggering a luminescent reaction cascade and light is finally with a CCD camera.

With respect to this technology, WO 04/69849 discloses a method of amplifying a plurality of nucleic acids (e.g., each sequence of a DNA library, transcriptome, or genome) in a rapid and economical manner in a single reaction tube. More particular, WO 04/69849 discloses a simultaneous clonal amplification (e.g., by PCR) of a plurality of samples (as many as several hundred thousand) in one reaction vessel. In this contest, WO 04/69849 provides a means for encapsulating a plurality of DNA samples individually in a microcapsule of an emulsion (i.e., a microreactor), performing amplification of the plurality of encapsulated nucleic acid samples simultaneously, and releasing said amplified plurality of DNA from the microcapsules for subsequent reactions. For example, single copies of the nucleic acid template species are hybridized to capture beads comprising, e.g., capture oligonucleotides or chemical groups that bind to the nucleic acid template. The beads are suspended in complete amplification solution and emulsified to produce microreactors (typically 100 to 200 microns in diameter). After this, amplification (e.g., PCR) is used to clonally increase copy number of the initial template species in the microreactors, and these copies bind to the capture beads in the microreactors. Alternatively, capture beads are added to an amplification reaction mixture comprising nucleic acid template and this mixture is emulsified to produce microreactors. Amplification (e.g., PCR) is used to clonally increase copy number of the initial template species in the microreactors, and these copies bind to the capture beads in the microreactors. Thus, the microreactors according to WO 05/03375 allow the simultaneous clonal and discrete amplification of many different templates without cross contamination of the amplified products or reagents, or domination of one particular template or set of templates (e.g., PCR bias).

However, according to WO 05/03375 it is necessary to perform an adaptor ligation step in which a plurality of different nucleic acid molecules is tagged with an adaptor sequence which may subsequently become bound to a bead with a covalently attached complementary adaptor sequence.

Another important DNA analysis technique is analytical polymerase chain reaction (PCR). Quantification of PCR, however, to date is based on analogous measurement modes. In some cases, however, a digital counting principle would be highly desirable for example in areas such as cancer detection: quantification of mutant alleles in an excess wild type background, detection of allelic imbalance, gene expression of rare transcripts and/or mutant alleles in transcripts, and viral detection and quantification.

Thus, the availability of a digital counting of DNA/cDNA/mRNA addresses unserved needs in molecular medicine, e.g. highly relevant for cancer diagnostics, circulating turner cells, pre-natal embryonic cells where a specific event has to be detected within a high background.

It was therefore an object of the present invention to provide an improved method and improved reagents for the simultaneous analysis of multiple nucleic acid molecules.

In a particular aspect it was an object of the present invention to provide a solid support or a plurality of solid supports which may be used to improve the sequencing workflow described above or enable digital PCR counting.

Various solid supports comprising immobilized nucleic acids such as beads comprising immobilized oligonicleotides are well known in the art. The exact design and configuration of these beads depends on the application for which they are used: G. Steinberg-Tatman et al (Bioconjugate Chemistry 2006, 17, 841-848) describe a method for synthesizing beads with two different oligonucleotides attached to the surface via a non cleavable linker. One oligonucleotide is used as a sequence specific capture probe the other as decoding sequence.

U.S. Pat. No. 5,639,603 describes beads with one or more immobilized oligonucleotide decoding tags.

Xu, X. et al., Journal of the American Chemical Society 128 (2006) 9286-9287 describe gold particles with two different oligonucleotides attached to the surface for building up ordered multiparticle nanostructures.

WO 2001062982 and U.S. Pat. No. 5,641,658 describe PCR on bead surfaces with two immobilized primers. The PCR method is named bridge amplification.

WO 2001012862 describes a method for generating a pool of oligonucleotides by cleaving different oligonucleotides which are attached to a substrate via different cleavable linkers.

WO 2007111937 describes an array for primer pairs where at least one primer is attached via a cleavable linkage for enrichment of genomic DNA used in sequencing.

KR 2007044677 describes beads with a first and a second immobilized PCR primer for use in emulsion PCR. The first primer is non cleavable. The release of the second primer is achieved by changing the pH value. Yet, changing the pH value has the disadvantage of potentially undesired side reactions and furthermore makes further processing of the sample more difficult.

SUMMARY OF THE INVENTION

Thus, the present invention is directed to a solid support comprising at least two sequence specific amplification primers wherein at least one primer is bound to said support with an inducible cleavable linker. Inducible cleavable in the context of the present invention means that the cleavage can be triggered by means of providing an external stimulus, which results in an immediate and essentially complete cleavage reaction. Preferably, said cleavable linker is a photo-cleavable linker.

In a first major embodiment, said solid support is a bead. Such a bead according to the present invention is composed of a material selected from the group consisting of silicon, titanium-dioxide, aluminum oxide, lanthanide oxide, glass, silicates, polystyrene, cellulose, sepharose and polyamide. A bead is either of one pure material or composed of two or more materials, whereas the two or more materials are mixed or assembled in a ordered manner like in core shell particles. The surface of a bead is functionalized in such a manner that oligonucleotides can be attached.

In a second major embodiment, the present invention is directed to a library of beads as disclosed above.

Preferably, each member of the plurality of primers which are bound to the bead via a cleavable linker carries a different detectable label or a unique mixture of multiple labels.

In a third major embodiment, the solid support is a microtiter or picotiter (PTP) plate comprising a plurality of wells, characterized in that a plurality of said wells comprises a surface with at least two sequence specific amplification primers wherein at least one primer is bound to said support with a cleavable linker.

Furthermore, the present invention is directed to methods for preparing any of the solid supports as disclosed above.

In particular, the present invention is directed to a method for preparing a solid support and preferably a bead comprising at least two sequence specific primers, further characterized in that at least one of said primers is cleavable, said method comprising the steps of providing a solid support carrying at least one or more functional groups, and reacting said one or more functional groups with the reactive group or groups of two sequence specific primers, wherein a cleavable reactive moiety is present either within one of the spacers connecting said solid support with its functional group or one of its functional groups or said cleavable moiety is present within one of the spacers connecting one of said sequence specific primers with its reactive group.

In a first embodiment, the method according to the present invention comprises the steps of providing a solid support comprising two functional groups each carrying a different protecting group, deprotecting a first functional group and reacting said group with the reactive group of a first primer, and deprotecting the second functional group and reacting said group of said bead with the reactive group of a second primer.

Said two functional groups are connected to the bead via two separate linkers, but in a particular embodiment, said two functional groups are connected to the bead via a two arm linker.

In a second embodiment the method according to the present invention comprises the steps of providing a solid support carrying exactly one functional group, deprotecting said functional group, and reacting said group with a mixture of a first and a second sequence specific primer, said first and second primers comprising identical reactive groups, characterized in that at least one of said primers is connected to its reactive group via a cleavable moiety.

In a third embodiment the method according to the present invention comprises the steps of providing a bead carrying exactly one functional group, and deprotecting said functional group and reacting said group with an oligonucleotide representing a first and a second amplification primer which are connected by a cleavable moiety.

In a fourth embodiment the method according to the present invention comprises the steps of providing a bead carrying protected OH groups, protected with two different orthogonal protecting groups, cleaving off one of said orthogonal protecting groups and synthesizing the first primer on the bead, and cleaving off the second of said orthogonal protecting group and synthesizing the second primer on the bead As it is known by the skilled artisan, orthogonal protecting groups can be selectively removed dependent on the conditions applied.

Figure 3A:
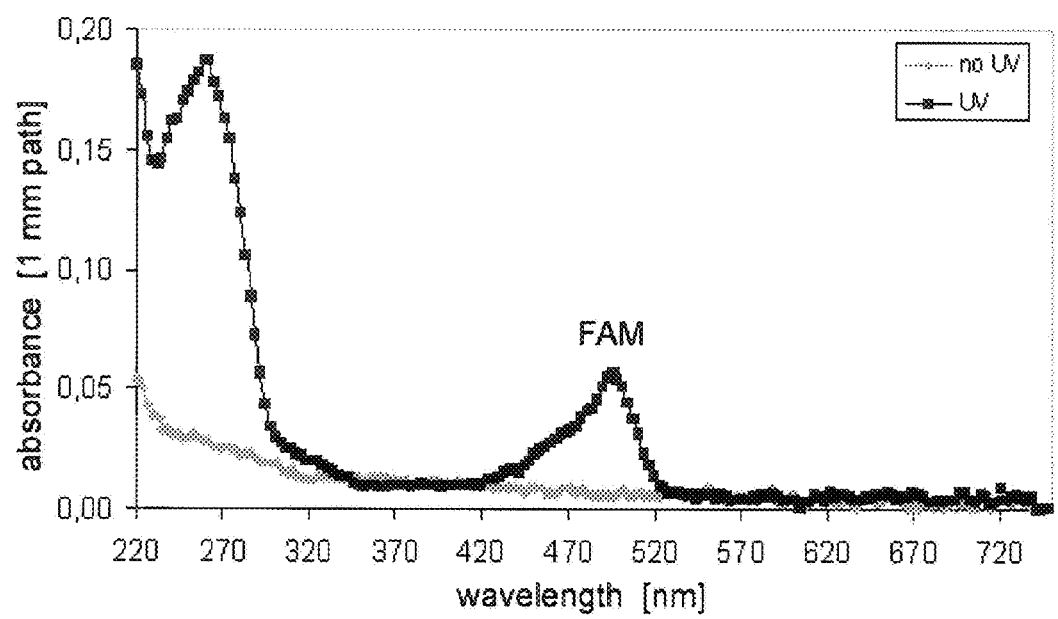
FIG. 3A-B: Absorbance measurement in FIG. 3A demonstrates the solubilization of a fluorescein-modified oligonucleotide probe (Sequence ID #1) when photolytically cleaved off sepharose beads.
Figure 3B:
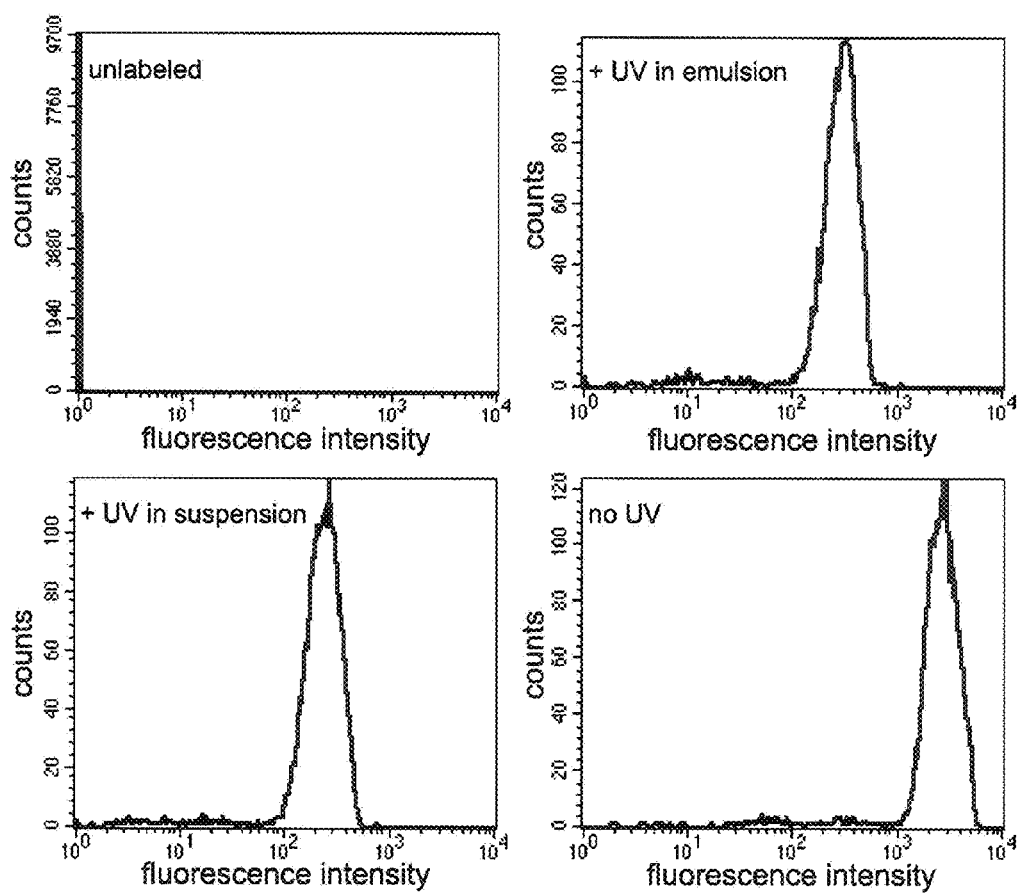

The flow cytometric measurement in FIG. 3B shows photocleavage indicated by decrease in fluorescence intensity when sepharose beads conjugated with fluorescein-modified oligonucleotide probes (Sequence ID #1) are subjected to a photocleavage reaction in suspension or emulsion.

Figure 4:
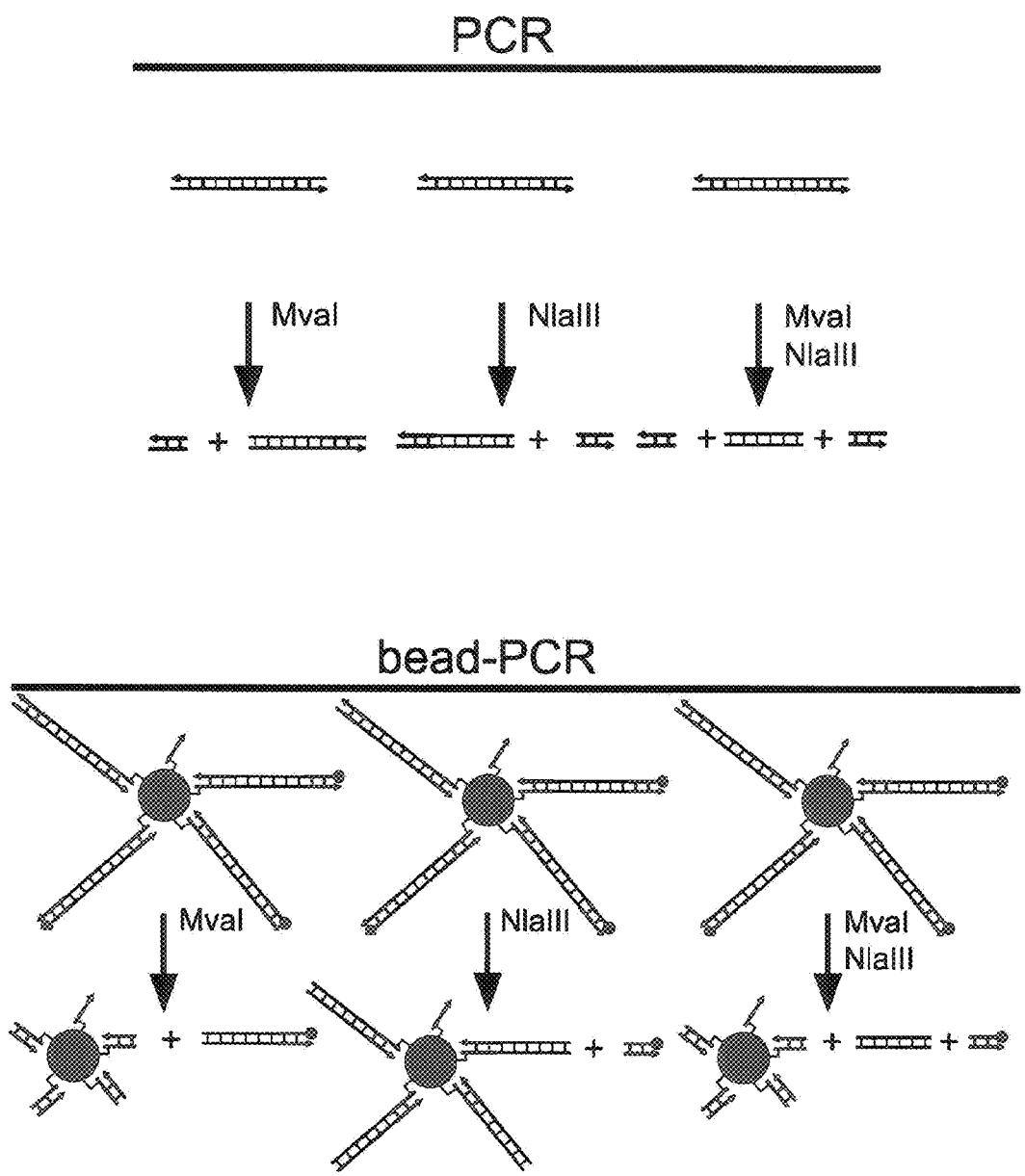

FIG. 4 illustrates the restriction endonuclease assay detecting conventional PCR products and PCR products immobilized to beads carrying stationary and photo-cleavable primer (Sequence ID #2, 3).

Figure 5:
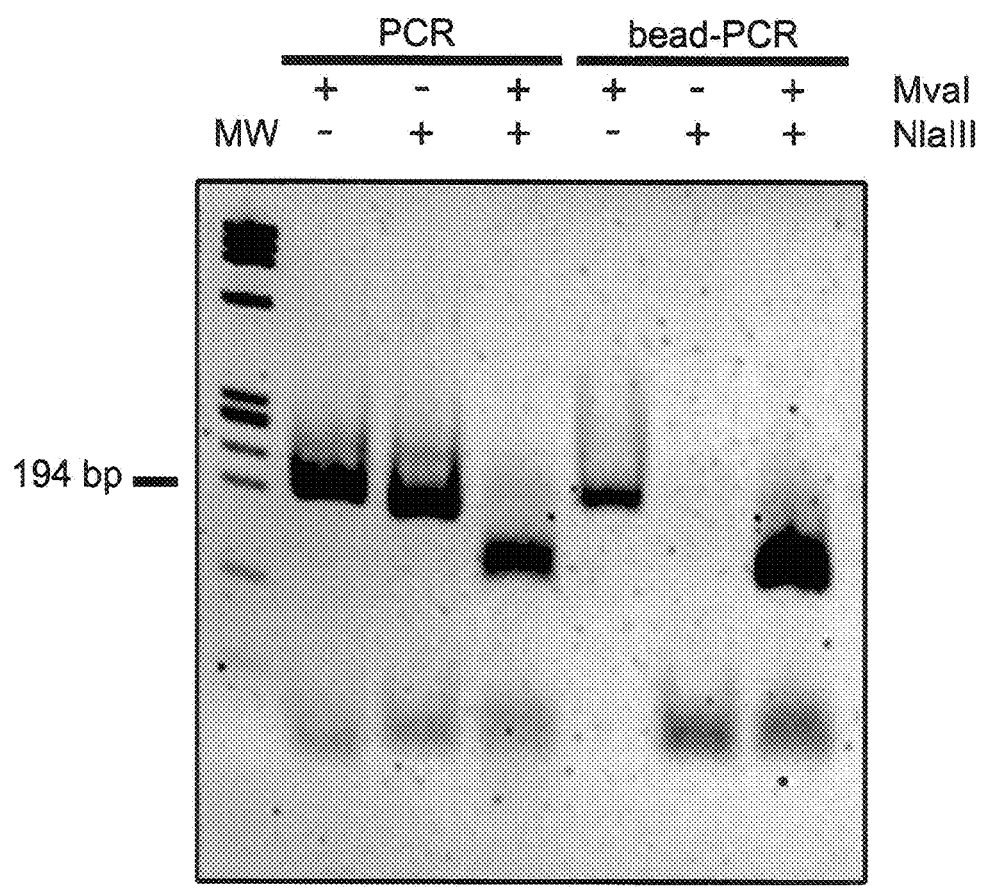

FIG. 5 shows the gel electrophoretic detection and identification of double stranded DNA obtained after conventional PCR or after PCR using bead immobilized primer (Sequence ID #2, 3) in suspension.

Figure 6:
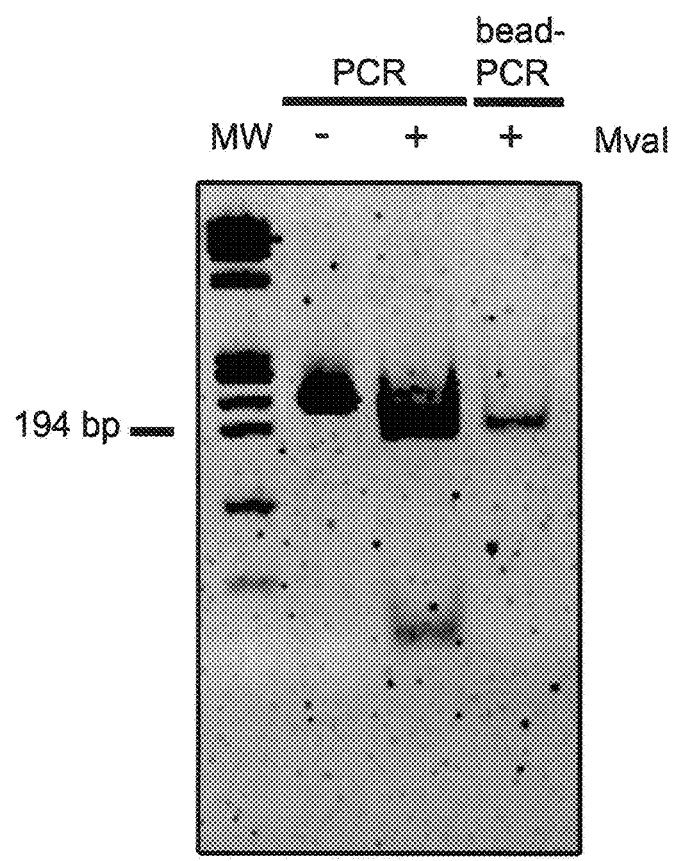

FIG. 6 shows the gel electrophoretic detection and identification of double stranded DNA obtained after conventional PCR or after PCR using bead immobilized primer (Sequence ID #2, 3) in emulsion.

Figure 7:
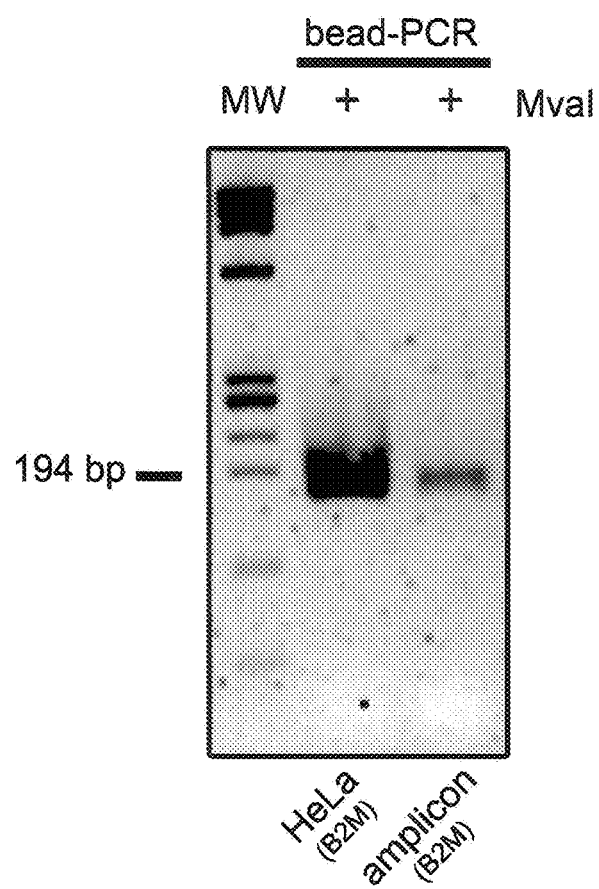

FIG. 7 demonstrates via restriction endonuclease treatment and gel electrophoresis that specific PCR products can be obtained with emulsion PCR and bead immobilized primer (Sequence ID #4, 5) using HeLa cDNA or an amplicon as template.

Figure 8:
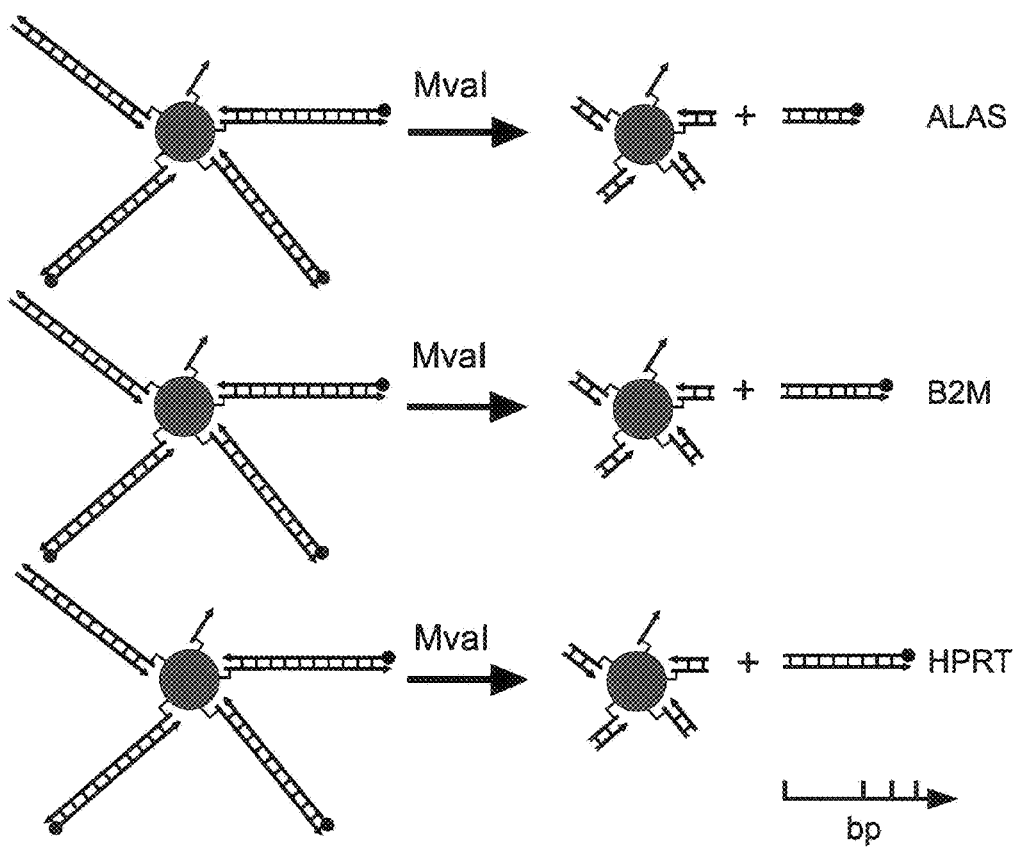

FIG. 8 illustrates the restriction endonuclease assay detecting PCR products immobilized to a set of distinct beads carrying stationary and photo-cleavable primer (Sequence ID #4-9) after multiplexed PCR.

Figure 9A:
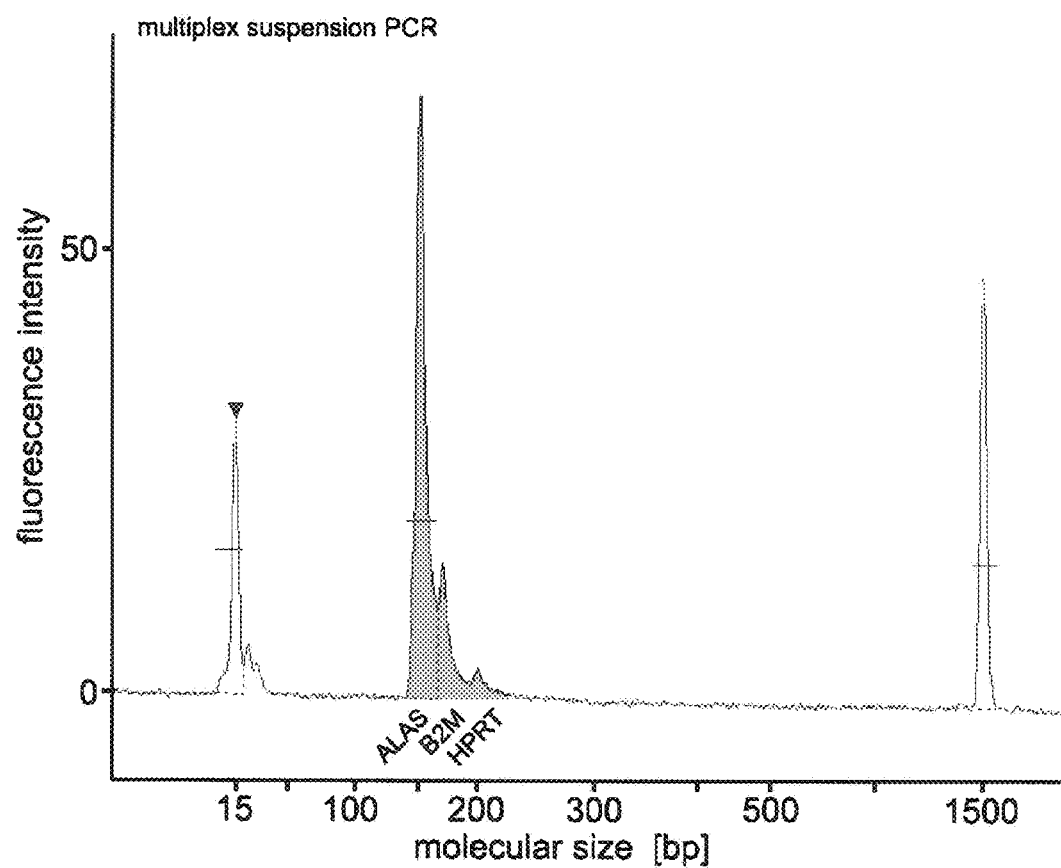
Figure 9B:
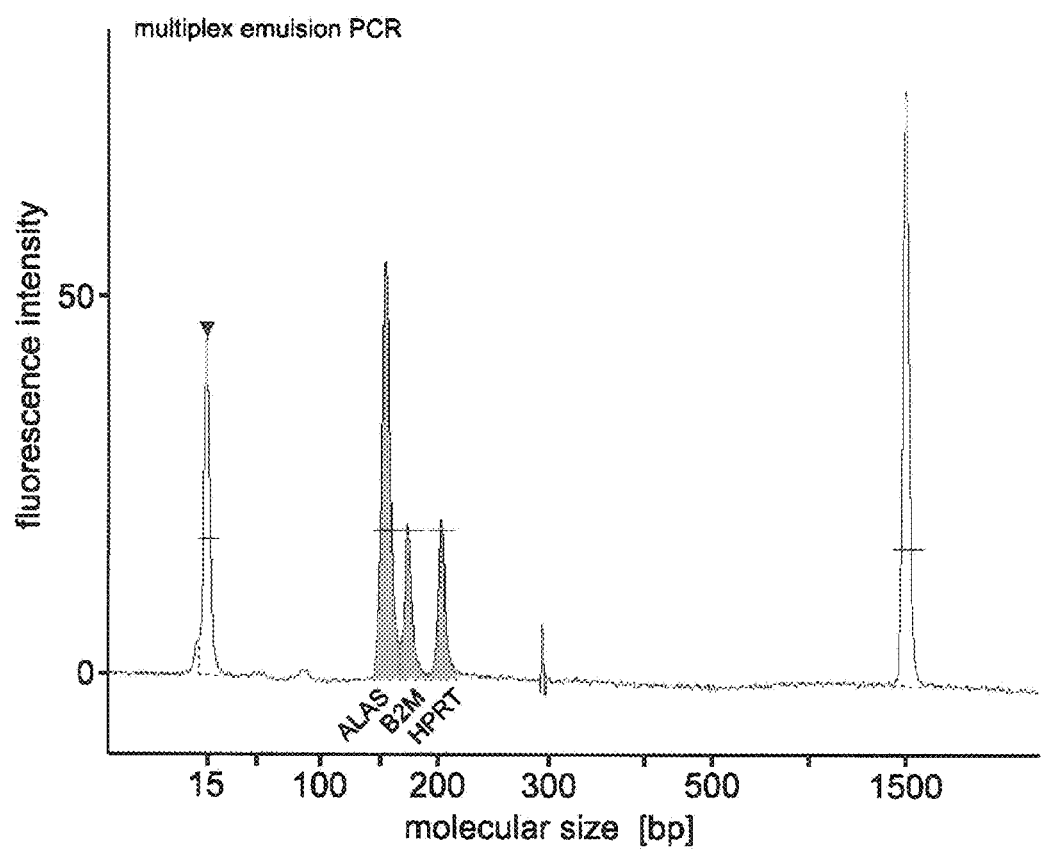

FIG. 9A-B: Electropherograms in FIGS. 9 A and B show the detection and identification of double stranded DNA obtained after multiplexed PCR using a set of distinct bead immobilized primer (Sequence ID #4-9) in suspension and in emulsion.

DETAILED DESCRIPTION OF THE INVENTION

Thus, the present invention is directed to a solid support comprising at least two sequence specific amplification primers wherein at least one primer is bound to said support with an inducible cleavable linker.

In particular, if said solid support is a bead, such a bead according to the present invention is especially useful for a method of analyzing a nucleic acid by means of contacting said nucleic acid with multiple beads comprising a pair of capture primers and subsequent amplification. In general, a method according to the present invention comprises the following three phases:
  selection of one or a mixed pool of sequences of interest by submitting target DNA to beads carrying each individual sequence specific capture molecules,
  statistically capturing 1 target molecule per bead, and
  amplification by PCR; the number of beads carrying amplified gene specific material being proportional to the number of sequence specific target molecules.

As a consequence, the present invention provides a possibility for highly parallel and miniaturized analysis of Nucleic Acids and includes applications such as qualitative and/or quantitative detection of genes of interest, gene expression analysis, mutation detection but is not limited to this.

In the context of the present invention, the following definitions shall apply:

"Multiple nucleic acid molecules" is understood as a population of molecules characterized in which at least two different nucleic acid sequences are represented. In most cases, a plurality of many different sequences is represented.

"Plurality of beads" is understood as a number of at more than 1000, preferably more than 10 000 and most preferably more than 100 000 beads "Pair of sequence specific amplification primers" is understood as two oligonucleotide molecules which together can act as a pair of amplification primers in such a way that during a nucleic acid amplification reaction, an amplification product with a defined length is generated.

"Cleavable linker" is understood as a chemical entity comprising a chemical bonding which upon a specific treatment can be resolved in such a way that the remaining parts of the molecule stay intact. Preferably, the cleavable linker is an "Inducible cleavable linker" which is defined as a cleavable linker which can be resolved by means of providing an external stimulus. A typical example for an inducible cleavable linker is a photocleavable linker, wherein the bonding is resolved by means of treatment with light of a defined wavelength.

"Capturing" is understood as (i) hybridizing a population of nucleic acid molecules with a specific nucleic acid sequence that is immobilized on a solid support such as a bead and which is at least partially complementary to a sequence of interest that may be represented within said population of nucleic acid molecules, and (ii) removal of unhybridized nucleic acid molecules from the formed hybridization complexes.

"Clonally isolating" is understood as separating a plurality of beads from each other such that each single bead is being placed at a different location. Preferably such a location is a micro- or picowell.

"Clonally amplifying" is understood that a population of nucleic acid molecules is being amplified in such a way that amplification products originating from different original target molecules are physically separated from each other. For example, all amplification products originating from the same original target nucleic acid molecule may be immobilized on a bead which enclosed in micelle.

"Emulsion" in the context of a present invention is understood as a water in oil emulsion, characterized in that small hydrophilic drops comprising a single bead are encapsulated in a micelle which is surrounded by a lipohilic liquid.

"Sequencing by synthesis" is understood as determining whether during a primer extension reaction, a specific nucleoside triphosphate has been incorporated which by itself can be elongated during the subsequent step of the primer extension reaction.

"Subjecting to a thermal gradient" is understood as heating or cooling a sample of interest starting from a first defined temperature and ending at a second defined temperature. The gradient may be either a continuous gradient which is preferably linear or alternatively a step-gradient. If PCR products or hybrids of nucleic acid probes and target molecules are subjected to such a gradient, a melting curve analysis or a monitoring of temperature dependence of hybridization can be performed.

"Real Time PCR" is understood as a polymerase chain reaction characterized in that the progress of the amplification reaction is monitored at least once within one amplification cycle. Preferably, amplification is monitored with either an intercalating fluorescent dye or alternatively, with amplicon specific nucleic acid hybridization probe such as for example a 5' Nuclease TaqMan probe, a Molecular Beacon probe, or a pair of FRET Hybridization Probes.

"Quenching" is understood as decreasing the emission of fluorescence from a fluorescent compound which is caused by a second chemical entity which is in close spatial vicinity to said fluorescent compound.

"Quantitative mutational analysis" is understood as a method comprising the steps of (i) screening of a plurality of nucleic acid molecules with essentially identical sequences for sequence variations, and (ii) determining the rate or the rates at which at least one or several of such sequence variations are present within said plurality of nucleic acid molecules. For example such sequence variations may be single nucleotide polymorphism.

Preparation of a Solid Support According to the Present Invention

The present invention requires the reversible covalent attachment of a first sequence specific amplification primer to a solid support via a flexible and cleavable linker molecule such that the primer can be hybridized to a target molecule and released into solution for target amplification and detection while a second sequence specific amplification primer stays covalently attached to the surface under cleavage conditions. The cleavable linker molecule can be cleavable by acid, base, light or any other means well known to those trained in the field. Preferably, it is exactly one primer which is bound to the bead via a cleavable linker.

In case the solid support is a bead or a plurality of beads, the beads have an average size of about 10 µm to about 250 µm. Preferably, the beads have an average diameter of about 20 to about 100 µm. Highly preferred, the beads have an average diameter of about 30 µm to 80 µm. For example, the beads may have an average diameter of about 40 µm.

The material of the beads to which the two primers shall be attached must be stable against oxidation and to hydrolysis, and may be inorganic e.g. silicon or titanium dioxide or aluminum oxide or glass; or organic e.g. polystyrene, cellulose, polyamide and others. A bead is either of one pure material or composed of two or more materials, whereas the two or more materials are mixed or assembled in a ordered manner like in core shell particles.

The surface of the beads may be porous or plain. The surface of a bead is functionalized in such manner that oligonucleotides can be attached. Therefore the surface of the beads has a functionalized surface comprising functional groups like amino-, thiol-, carboxyl-, maleinimido-, azido-, alkin-, hydrazine-, hydroxylamino-, keto- and aldehyde-groups, triazinchloride-, quinones-, diene-, or other reactive functions known by those trained in the field.

The corresponding functional moiety of the primer can be selected from a group consisting of carboxy-, aldehyde-, azide-, alkyne-, amino-, thiol-, maleinimido-, sulfonylalken-, iodacetyl-, amino hydrazine-, hydroxylamino-, and maleinimido-.

More precisely, the corresponding modification of the oligonucleotide is determined by the surface functional group and vice versa as can be seen in the following table:

TABLE 1

| Functional group of the oligonucleotide | Functional group required on the bead |
|---|---|
| amino | carboxy or aldehyde |
| alkyne | azide |
| Azide | alkyne |
| hydrazine or hydroxylamino | aldehyde, keto or carboxy |
| triazinchlorid | amino or thiol |
| thiol | maleinimido sulfonylalken or iodacetyl |
| aldehyde or keto | amino hydrazino hydroxylamino |
| quinones | amino |
| dienes | maleinimido |

The functional group is either introduced on the surface eg by silanization of glass-silicacte lanthanide-oxides with an modified silane or the bead by itself contains a priori functional groups which are created during production of the bead eg by copolymerization of polystyrene and an appropriate alkene containing the functional group. A priori present functional groups could be transformed in another functional group by using heterobifunctional linkers. Such linker could be cleavable or noncleavable. By this procedure beads with different orthogonal functionalities can be created.

Orthogonal means that a first functional group reacts with a first modified oligonucleotide in the presence of a second functional group which reacts simultaneously with the second modified oligonucleotide. A pair of such functional groups is succinylamidocarboxy and alkin, which requires an amino and azido modified oligonucleotide.

Sequential attachment of two different oligonucleotides to the same type of surface functional group is achieved by using orthogonal protective groups, (G. Steinberg-Tatman et al Bioconjugate Chemistry 2006, 17, 841-848)

If the bead is a gold particle or the bead is coated with a metal film eg with gold thiol modified oligonucleotides are directly reacted with the surface.

General methods for covalently binding a primer onto a solid support are well known in the field. For example, Primer oligonucleotides are first synthesized by standard Phosphoramidate chemistry. Such a synthesized primer can be further modified with a cleavable linker molecule either during or subsequent to the oligonucleotide synthesis. Attachment of a cleavable primer and a non-cleavable primer can be achieved by any means of multiple well known attachment chemistries described in the literature for microarray technologies or any other known method. Examples are disclosed and reviewed in Wittebolle, L. et al., Journal of Chemical Technology and Biotechnology 81 (2006) 476-480, Steinberg, G. et al., Biopolymers 73 (2004) 597-605, Di Giusto, D. A. et al., Topics in Current Chemistry 261 (2005) 131-168, and Zatsepin, T. S. et al., Bioconjugate Chemistry 16 (2005) 471-489.

The solid support and preferably the bead which according to the present invention comprises at least two sequence specific primers, wherein at least one of said primers is cleavable, is prepared in a new unpredicted manner of combining different steps of solid phase chemistry and oligonucleotide synthesis which as single steps per se are already known in the art. Thus the solid support according to the present invention is prepared by a method comprising the steps of providing a solid support carrying at least one or more functional groups, and reacting said one or more functional groups with the reactive group or groups of two sequence specific primers, wherein a cleavable reactive moiety is present either within one of the spacers connecting said solid support with its functional group or one of its functional groups or said cleavable moiety is present within one of the spacers connecting one of said sequence specific primers with its reactive group.

There are at least six alternatives to produce such a solid support:

(i) In a first embodiment, the method according to the present invention comprises the steps of providing a solid support comprising two independent functional groups each carrying a different protecting group, deprotecting a first functional group and reacting said group with the reactive group of a first primer, said primer characterized in that it carries a cleavable moiety between its reactive group and the nucleotide sequence itself, and deprotecting the second functional group and reacting said group of said bead with the reactive group of a second primer.

(ii) In a second embodiment, the method according to the present invention comprises the steps of
- providing a solid support comprising two independent functional groups each carrying a different protecting group, wherein one of said functional group is connected to the solid support via a cleavable moiety,
- deprotecting a first functional group and reacting said group with the reactive group of a first primer, and
- deprotecting the second functional group and reacting said group of said bead with the reactive group of a second primer.

(iii) In a third embodiment, the method according to the present invention comprises the steps of
- providing a solid support comprising two functional groups each carrying a different protecting group said functional groups being connected to the solid support via a branched linker,
- deprotecting a first functional group and reacting said group with the reactive group of a first primer, said primer characterized in that it carries a cleavable moiety between its reactive group and the nucleotide sequence itself, and
- deprotecting the second functional group and reacting said group of said bead with the reactive group of a second primer.

(iv) In a fourth embodiment, the method according to the present invention comprises the steps of
- providing a solid support comprising two functional groups each carrying a different protecting group said functional groups being connected to the solid support via a branched linker, wherein one of said functional group is connected to the solid support via a cleavable moiety,
- deprotecting a first functional group and reacting said group with the reactive group of a first primer, and
- deprotecting the second functional group and reacting said group of said bead with the reactive group of a second primer.

(v) In a fifth embodiment, method according to the present invention comprises the steps of
- providing a solid support carrying exactly one functional group,
- deprotecting said functional group, and
- reacting said group with a mixture of a first and a second sequence specific primer, said first and second primers comprising identical reactive groups, characterized in that at least one of said primers is connected to its reactive group via a cleavable moiety.

(vi) In a sixth embodiment the method according to the present invention comprises the steps of
- providing a bead carrying exactly one functional group, and
- deprotecting said functional group and reacting said group with an oligonucleotide representing a first and a second amplification primer which are connected by a cleavable moiety.

Different types of linkers can be used to prepare beads according to the invention. Amino-modified linkers, biotin-modified linkers which can be used to attach amino groups or biotin to a terminus of an oligonucleotide, and internal photocleavable linkers which can be used in combination with any other modifier.

Cleavable linkers are well known in the art and can be discriminated into two classes. The first class requires a reactive species eg a reductive species or OH− or H+ in order to achieve cleavage. Examples are disulfide bridges which could be cleaved by reduction with thiols or baselabile "linkers" like an RNA monomer incorporated at the terminus of an oligonucleotide. The second class is cleaved by physical means eg by irradiation such as illumination or heating.

Photocleavable linkers are linkers wherein a covalent bond is broken by means of irradiation with light. The irradiation wavelength has to be chosen in such a manner that the nucleobases of the attached oligonucleotides do not absorb in order to avoid side reactions like T-T dimerization or photooxidation. If organic dyes are attached to the bead, eg within a detection probe the irradiation wavelength does not match absorption of such dyes.

Typically and suitable photocleavable linkers are for example derived from orthonitrobenzylalkohols, and are well known in the literature. The photocleavage is achieved by irradiation with UV light of the wavelength>340 nm.

Photocleavable linkers which can be introduced during oligonucleotide synthesis are exemplarily described in the following references: WO 92/002528, WO 07/082,713, U.S. Pat. No. 5,258,506, Olejnik, J. et al., Nucleic Acids Research 26 (1998) 3572-3576, Hausch, F. and Jaeschke, A., Nucleic Acids Research 28 (2000) 28, e35, Hausch, F., and Jaeschke, A., Tetrahedron 57 (2001) 1261-1268, Wenzel, T. et al., Nucleosides, Nucleotides & Nucleic Acids 22 (2003) 1579-1581, Dell'Aquila, C. et al., Tetrahedron Letters 38 (1997) 5289-5292, Ordoukhanian, P. and Taylor, J.-S., Journal of the American Chemical Society 117 (1995) 9570-9571, Saran, D. et al., Bioconjugate Chemistry 18 (2007) 275-279, and Piggott, A. M., and Karuso, P., Tetrahedron Letters 46 (2005) 8241-8244.

A particular mode of indirect photocleavage can be achieved by photogenerating of reactive species like $H^+$ or $OH^-$ whereas the formation of such reactive species results in cleavage of a base or acid labile covalent bond. WO 2006117556 and WO 9941007 describe methods for photo-generation of acids and bases. Base or acid labile linkers are well known in the art (e.g., Chitkul, B., Tetrahedron Letters 42 (2001) 6211-6214).

A thermally-cleavable linker is described in Keller, K. A., Tetrahedron Letters 46 (2005) 1181-1184.

Immobilized oligonucleotides are in either case attached to the surface in such a manner that initial target capturing is facilitated and that the PCR is still efficient even with one immobilized primer. This is achieved by allowing sufficient spacing between the bead surface and the primer sequence. Therefore long linkers like PEG-linkers or multiple short linkers are attached to the oligonucleotides. A second parameter influencing capturing is the surface loading density on the bead, which could be controlled by an appropriate bead production process or by diluting the oligonucleotides to be immobilized with non nucleotidic compounds having the same functional group as the oligonucleotide to be immobilized.

Usage of a Solid Support According to the Present Invention.

As mentioned above, the solid support to the present invention may be a bead or a plurality of beads. Beads according to present invention may be used within a method for analyzing multiple nucleic acid molecules of interest comprising in the following steps
a) providing a plurality of beads, characterized in that each bead comprises at least one pair of sequence specific amplification primers, further characterized in that at least one of said primers is bound to the bead via a cleavable linker,
b) capturing the nucleic acid molecules of interest from a sample,
c) clonally isolating said plurality of beads, d) cleaving said at least one primer,
e) clonally amplifying said nucleic acid thereby creating multiple amplification products, and
f) analyzing said amplification products.

Figure 1:
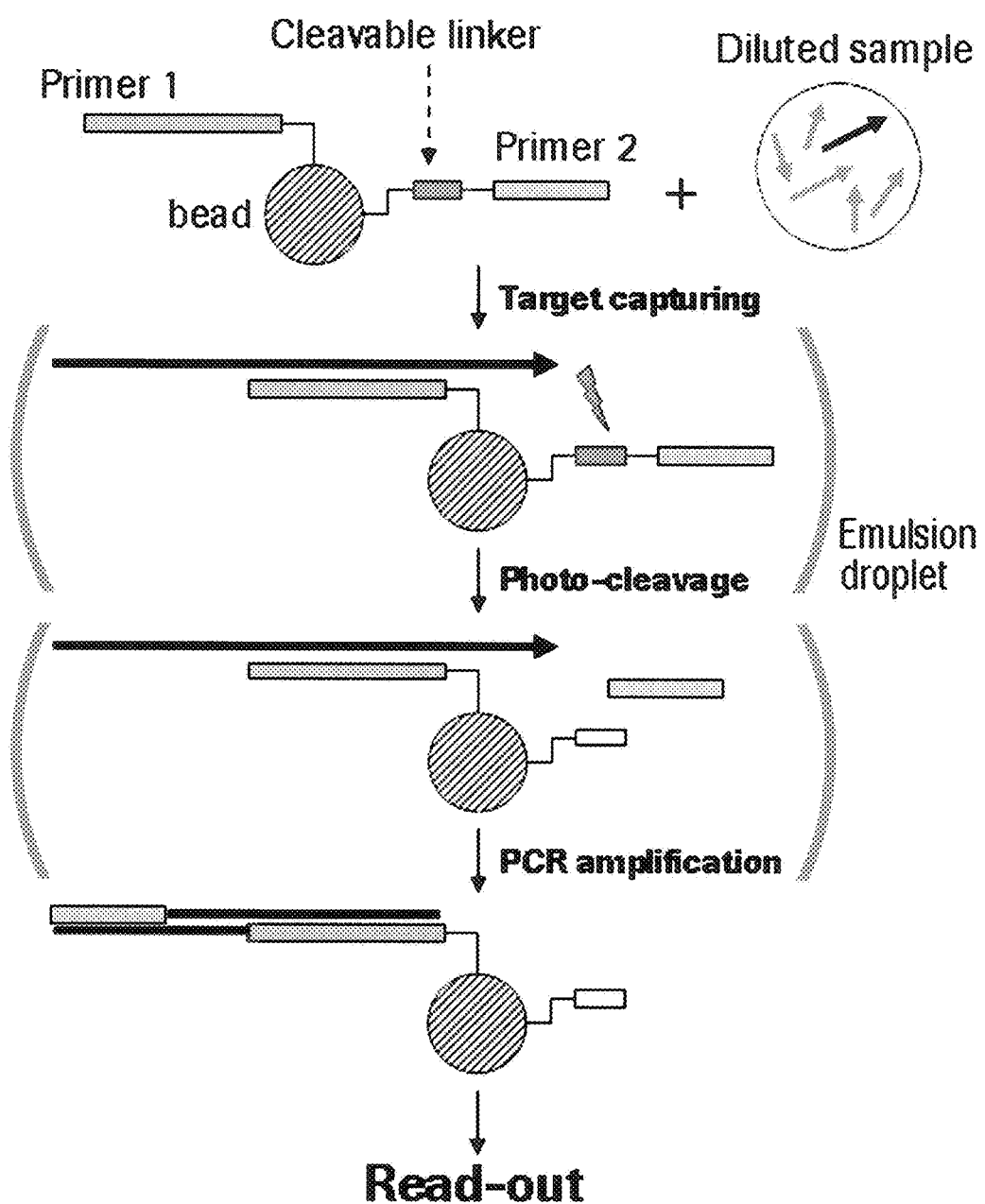
FIG. 1 illustrates the assay principle based on primers that are specific for the target nucleic acid and immobilized on a coded solid carrier (e.g. bead). The stationary primer 1 is used for target capturing, whilst primer 2 will be photolytically cleaved off the carrier to drive clonal PCR amplification of the captured target in emulsion.

An exemplary overview is shown in FIG. 1: A sample is subjected to a population of beads comprising a pair of amplification primers, one of which is photo-cleavable (steps a, b). Clonal amplification is achieved by means of performing an emulsion PCR (steps c, d, e). Subsequently, the amplification products are becoming analyzed (step f).

In detail, the general steps are performed as follows:

a) Providing a Plurality of Beads

Preparation of said beads has been disclosed in detail above.

b) Capturing the Nucleic Acid Molecules of Interest from a Sample

Target molecules are then hybridized to the beads containing the cleavable and non-cleavable primer. Suitable hybridization conditions with respect to the appropriate buffer system and appropriate hybridization temperatures are well known in the art and can be optimized according to the specific conditions such as the lengths and sequences of the specially used amplification primers. Preferably hybridization is done using a molar excess of beads compared to the sequence or sequences which shall be amplified in order to capture as many target nucleic acids as possible. In particular, a molar excess of 1:5-1:100 and preferably 1:10-1:50 has been proven to be particular advantageous. If multiple different target sequences shall be detected and/or analyzed, then a library of beads with accordingly different multiple primer pairs has to be used.

c) Clonally Isolating Said Plurality of Beads

Clonal isolation is a prerequisite in order to obtain quantitative data with respect to sequence variations that are present in the plurality of nucleic acid molecules which are being analyzed. In principle, there are two different modes of clonal isolation.

In a first embodiment, PCR reagents such as the thermostable DNA polymerase, the deoxynucleoside triphosphates and an appropriate buffer are first added to the beads. Subsequently, a water-in-oil emulsion is generated characterized in that each bead is encapsulated in a single micelle containing an aqueous solution which allows for a nucleic acid amplification reaction. Appropriate conditions are for example disclosed in WO 04/069849.

In a most preferred embodiment, about 3000 beads are contained within 1 microliter of a 1:2 water to oil emulsion.

In a second alternative embodiment, step c) comprises the distribution of said plurality of beads into the cavities of a micro- or picotiter plate. The size of the cavities corresponds to the diameter of the beads in such way that one cavity can only be filled with one bead.

Distribution of the beads into the cavities can be obtained for example by means of constant agitation, smooth shaking or means of centrifugation. The PCR reagents such as the thermostable DNA polymerase, the deoxynucleoside triphosphates and an appropriate buffer are added either prior or preferably subsequently to the distribution of the beads into the cavities of the micro- or picotiter plate. Alternatively addition of said PCR reagents can be performed after step d).

d) Cleaving Said at Least One Primer

The beads comprising said primer which is bound via a cleavable linker are then exposed to cleavage conditions in order to cut the linker attaching the cleavable primer to the bead. In case clonal isolation has been achieved by means of distribution of said plurality of beads into the cavities of a micro- or picotiter plate, the cleavable linker molecule can be cleavable by acid, base, light or any other means well known to those trained in the field. Preferably, the linker is a photo-cleavable linker because addition of an additional reagent is avoided.

In case clonal isolation has been achieved by means of generating a water-in-oil emulsion, it is even required to use a cleavage method, which is based on photo-activation. In this regard, there are several methods known in the art.

e) Clonally Amplifying Said Nucleic Acid Thereby Creating Multiple Amplification Products The reaction mixtures are then exposed to an appropriate thermocycling protocol in order to perform a nucleic acid amplification reaction. The still immobilized (non-cleavable) amplification primer hybridizes to the target nucleic acid molecule as well as to the amplified products thereby holding them at the surface of the bead. The amplification primer which has been cleaved off the bead is capable of moving free in solution, such that an effective amplification reaction can be performed.

As a consequence, the present invention also provides for a method for producing a plurality of nucleic acid template-carrying beads wherein each bead comprises up to and more than 1,000,000 copies of a single nucleic acid sequence. Under optimized conditions, each bead may comprise over 20 million copies of a single nucleic acid.

In order to avoid the generation of unspecific amplification products, it is highly advantageous to apply a so called hot start PCR protocol. Several methods are known in the art. For example, it is possible to use DNA polymerase is reversibly inactivated as a result of a chemical heat labile modification. (U.S. Pat. No. 5,773,258, U.S. Pat. No. 5,677,152). An alternative approach to achieve heat labile inhibition of Taq DNA polymerase is the addition of monoclonal antibodies raised against the purified enzyme (Kellogg, D. E., et al., Biotechniques 16 (1994) 1134-7). Alternatively, short double stranded DNA fragments (Kainz, P., et al., Biotechniques 28 (2000) 278-82) or oligonucleotide Aptamers may be added to the reaction mixture (U.S. Pat. No. 5,693,502), (Lin, Y. and Jayasena, S. D., J. Mol. Biol. 271 (1997) 100-11) in order to generate a hot start effect. Still alternatively, EP 0 799 888 discloses an addition of 3' blocked oligonucleotides to PCR reactions. Due to the 3' block, these oligonucleotides can not act as primers. The blocked oligonucleotides are designed to compete/interact with the PCR primers which results in reduction of non-specific products. Another alternative is the use of phosphorothioate oligonucleotide primers in combination with an exonuclease III in the PCR reaction mixes (EP 0 744 470). In this case, a 3' exonuclease, which usually accepts double stranded as well as single stranded DNA substrates, degrades duplex artefacts such as primer dimers as well as carry over amplicons, while leaving the single stranded amplification primers undegraded. Similarly, the usage of primers with a basic modified 3' ends and template dependent removal by *E. coli* Endonuclease IV has been suggested (U.S. Pat. No. 5,792,607). A particular embodiment of the general idea is found in EP 1 275 735. Its specification discloses a composition for performing a nucleic acid amplification reaction comprising (i) a thermostable DNA-Polymerase, (ii) a thermostable 3'-5' Exonuclease, and (iii) at least one primer for nucleic acid amplification with a modified 3' terminal residue which is not elongated by said thermostable DNA-Polymerase as well as methods for performing a PCR reaction using this composition.

In a particular, the clonal amplification may be performed in the in the form of an allele specific PCR. In this detection method variant-specific amplification primers are used during the amplification which usually have a discriminating terminal nucleotide residue at the 3' terminal end of the primer which is only complementary to a special variant of the target nucleic acid to be detected. U.S. Pat. No. 5,595,890 for example describes such methods for allele-specific amplification and their use to detect clinically relevant point mutations for example in the k-ras oncogene. U.S. Pat. No. 5,521, 301 also describes methods for allele-specific amplification for genotyping the AB0 blood group system. In contrast U.S. Pat. No. 5,639,611 discloses the use of allele-specific amplification in connection with the detection of the point mutation responsible for sickle cell anemia. Such methods for detecting sequence variants, polymorphisms and, above all, point mutations require an allele-specific amplification particularly when the sequence variant to be detected is present in a lower amount compared to a variant of the same section of nucleic acid (or of the same gene) that is present in excess. This situation for example occurs when the aim is to detect disseminating tumour cells in body fluids such as blood, serum or plasma with the aid of allele-specific amplification (U.S. Pat. No. 5,496,699). For this purpose the DNA is firstly isolated from body fluids such as blood, serum or plasma which is composed of a relatively small amount of DNA from disseminating tumour cells and an excess of DNA from non-proliferating cells. Hence mutations in the k-Ras gene that are significant for tumoral DNA have to be detected on the basis of a few copies of tumoral DNA in the presence of an excess of wild type DNA.

f) Analyzing Said Amplification Products

In case clonal isolation of step c) has been achieved by means of generating a water-in-oil emulsion, it is required that in a first step, the plurality of beads carrying the amplification products is distributed into the cavities of a micro- or picotiter plate Subsequently there exist two alternative embodiments for analysis of the generated amplification products.

(i) Sequencing

In a first embodiment, the DNA bound to each bead may be subjected to a sequencing reaction. Preferably, said sequencing reaction is a sequencing by synthesis reaction, characterized in that incorporation of specific deoxynucleoside into the nascent DNA strand of a primer extension reaction is being monitored. Most preferably, said sequencing by synthesis reaction is a pyrophosphate sequencing reaction, wherein said incorporation is being monitored by means of detecting the generation of pyrophosphate (EP 932 700, U.S. Pat. No. 6,210,891).

By means of providing sequence specific beads, the pre-amplification of a certain target by PCR which is necessary according to methods known in the art is avoided. Instead, according to the present invention, the emPCR itself is performed with multiple beads, but all beads are carrying the same pair of amplification primers. More precisely, the beads have one immobilized forward and backward primer, both specific for the same gene. The non-cleavable primer may have an additional sequence at the 5'-end followed by a gene specific priming sequence. The cleavable primer has a specific sequence at the 5'-end, which prior to the sequencing reaction may act as a sequencing primer binding site. The 3' part of said cleavable primer is followed by a gene specific sequence. It is less preferred but still within the scope of the present invention, if the sequence corresponding, to the sequencing primer binding site is present at the 5' end of non-cleavable primer.

Many different beads, each containing primer pairs for different genes can be pooled. The target is then hybridized onto the beads in a capturing reaction. Subsequently, an emulsion suited for emPCR is generated. The emulsion then is submitted to conditions that cleave the cleavable linker. The beads then are subjected to "clonal amplification" by emPCR. After breaking of the emulsion and washing, the beads are physically separated on a picotiter plate and the amplification product is decoded/detected and/ or quantified by sequencing, for example with the Genome Sequencer FLX instrument (Roche Applied Science Cat. No. 04 896 548 001).

Summarizing, the main advantages are
that the target can be directly added to the beads
no pre-amplification of the genes or amplicons of interest is needed There is a possibility to supply a pool of sequence specific capture beads. The pools of sequence specific capture beads may be grouped into specific applications such as gene expression of oncology relevant genes and others.

(ii) End Point PCR Analysis

In a second alternative embodiment, the amplified DNA which is still bound to the bead may be analyzed directly by appropriate detection means. In other words: a PCR assay is performed characterized in that the generation of the amplicon is subject to an end-point measurement.

The beads have an immobilized forward and backward primer, both specific for one gene or nucleic acid sequence region of interest. One of the primers is cleavable, and the second primer is non-cleavable. Many different beads, each containing primer pairs for different genes/sequences are pooled. The target nucleic acid sample is hybridized onto the beads in a capturing reaction. An Emulsion suited for emPCR is generated. The emulsion is then submitted to conditions that cleave the cleavable linker. Subsequently, the beads are subjected to "clonal amplification" by emPCR. After breaking of the emulsion and washing the beads are physically separated on a PTP (picotiter plate) and the amplification product is detected in an end-point assay. In a particular embodiment, said detection is performed by means of subjecting the generated amplicons to a thermal gradient. As a consequence, it is possible to perform a melting curve analysis. (U.S. Pat. No. 6,174,670, U.S. Pat. No. 5,871,908).

The amplification products are preferably detected by means of fluorescence. For example, the amplification mix may already contain a double stranded nucleic acid binding moiety such as a fluorescent DNA binding dye which emits a corresponding fluorescence signal upon interaction with the double-stranded nucleic acid after excitation with light of a suitable wavelength. The dyes SybrGreenI and SybrGold (Molecular Probes) or dyes as disclosed in WO 2004/038038 have proven to be particularly suitable for this application. Other intercalating dyes can alternatively be used Due to the fact that amplicon detection with SybrGreen format can not discriminate between specific products and amplification artefacts such as primer/dimers, a subsequent melting curve analysis is usually performed. After completion of the PCR-reaction, the temperature of the sample is constitutively increased, and fluorescence is detected as long as SybrGreen is bound to the double stranded DNA present in the samples. Upon dissociation of the double stranded DNA the signal decreases immediately. This decrease is monitored with an appropriate fluorescence versus temperature-time plot such that a first derivative value can be determined, at which the maximum of fluorescence decrease is observed. Since primer/dimer double stranded DNAs are usually short, dissociation into single stranded DNA occurs at lower temperatures as compared to the dissociation of the double stranded specific amplification product.

Alternatively, the amplification mix may contain already one or more hybridization probes which are labeled with at least one fluorescent moiety. In this context of the present invention, molecular beacons, FRET hybridization probes and single labeled probes are particularly useful.

Molecular Beacon hybridization probes are labeled with a first component and with a quencher, the labels preferably being located at both ends of the probe. As a result of the secondary structure of the probe, both components are in spatial vicinity in solution. After hybridization to the target nucleic acids both components are separated from one another such that after excitation with light of a suitable wavelength the fluorescence emission of the first component can be measured (U.S. Pat. No. 5,118,801).

The FRET Hybridization Probe test format is especially useful for all kinds of homogenous hybridization assays (Matthews, J., A., and Kricka, L., J., Analytical Biochemistry 169 (1988) 1-25). It is characterized by two single-stranded hybridization probes which are used simultaneously and are complementary to adjacent sites of the same strand of the amplified target nucleic acid. Both probes are labeled with different fluorescent components. When excited with light of a suitable wavelength, a first component transfers the absorbed energy to the second component according to the principle of fluorescence resonance energy transfer such that a fluorescence emission of the second component can be measured when both hybridization probes bind to adjacent positions of the target molecule to be detected. Alternatively to monitoring the increase in fluorescence of the FRET acceptor component, it is also possible to monitor fluorescence decrease of the FRET donor component as a quantitative measurement of hybridization event.

The Single Labeled Probe consists of a single oligonucleotide labeled with a single fluorescent dye at either the 5'- or 3'-end (WO 02/14555). Two different designs can be used: G-Quenching Probes and Nitroindole-Dequenching probes. In the G-Quenching embodiment, the fluorescent dye is attached to a C at oligo 5'- or 3'-end. Fluorescence decreases significantly when the probe is hybridized to the target, in case two G's are located on the target strand opposite to C and in position 1 aside of complementary oligonucleotide probe. In the Nitroindole dequenching embodiment, the fluorescent dye is attached to Nitroindole at the 5'- or 3'-end of the oligonucleotide. Nitroindole somehow decreases the fluorescent signaling of the free probe. Fluorescence increases when the probe is hybridized to the target DNA due to a dequenching effect.

All hybridization probes disclosed above are used for melting curve analysis. In such an assay, the target nucleic acid is amplified first in a typical PCR reaction with suitable amplification primers. The hybridization probes may already be present during the amplification reaction or added subsequently. After completion of the PCR-reaction, the temperature of the sample is constitutively increased, and fluorescence is detected as long as the hybridization probe was bound to the target DNA. At melting temperature, the hybridization probes are released from their target, and the fluorescent signal is decreasing immediately down to the background level. This decrease is monitored with an appropriate fluorescence versus temperature-time plot such that a first derivative value can be determined, at which the maximum of fluorescence decrease is observed.

In case of an application characterized in that only one, two or a few different target genes are being amplified, it is possible to discriminate the different amplification products by means of subjecting the generated amplicons to a thermal gradient and perform a melting curve analysis. Using the SybrGreen detection format, it is easily possible to discriminate between at least two different amplicons Using a hybridization probe based detection format, it is easily possible with one or more hybridization probes labeled with the same fluorescent compound or compounds to discriminate between at least 4 different amplicon sequence variations which are amplified by the same or different amplification primers. In case different labels are used for different hybridization probes, it is possible to discriminate between respectively more different amplicon sequence variations.

According to the present invention there is also another scenario for detection which is based on the introduction of detectable tags. Therefore, the present invention provides a bead or a plurality of beads comprising at least two sequence specific amplification primers wherein at least one primer is bound to said support with a cleavable linker, and said primer further comprises a detectable tag.

In particular, the present invention also provides a library of beads, wherein each bead comprises a different pair of two sequence specific amplification primers wherein at least one primer is bound to said support with a cleavable linker, and said primer further comprises a detectable tag. In a very particular embodiment, the bead is the tag by itself or is modified on the surface with measurable tags.

In this context, beads carrying specific primer sequences are encoded with any kind of detectable tag that allows the specific detection of the beads. For example, the detectable tag can be a mass-tag, a fluorescence or color label or an e-Tag or a Raman tag, but is not limited to this. Further examples are haptens like Digoxygenin or Biotin or small peptides, all of which are detectable by an antibody.

For each sequence specific bead another tag or a specific number of a plurality of tags can be chosen that codes either by different color, different mass or others for the bead bound specific sequence. Depending on the number of different available labels, multiple target sequences can be analyzed.

Preferably, the primer which is bound to the bead via a cleavable linker carries a detectable tag. After cleaving and elongating the "cleavable"-primer the tag is incorporated into the PCR product on the beads and can be detected. Beads containing amplified product of different sequences can be differentiated and can be counted, thus enabling the possibility to qualitatively and quantitatively detect specific sequences. Thus, most preferably, each member of the plurality of primers which are bound to the bead via a cleavable linker carries a different detectable tag or plurality of tags.

In case of labeling the cleavable primer with a fluorescence tag this can be done in a way that the label is quenched as long as it is not elongated by polymerase to form a PCR amplicon. One envisaged quenching mechanism is using primers similar to single labeled hybridization probes wherein a dequenching occurs upon interaction with the a complementary target strand. Alternatively, primers could be used which are similar to molecular beacons, wherein a dequenching occurs upon linearization of oligonucleotide. As a consequence, the use of quenched primers minimizes the possibility of any background fluorescence signaling.

In case the cleavable primer is labeled with a hapten tag such as Biotin and Digoxygenin, the amplification product can be detected by chemiluminescence reaction using Avidin or Anti-Dig in a respective subsequent chemiluminescence reaction. In a particular embodiment, each member of the plurality of primers which are bound to the bead with a cleavable linker carries a different number of biotin or Dig labels that can be detected in a reaction cascade by fluorescence or chemiluminescence Therefore a POD streptavidin and an AP anti Dig conjugate in combination with fluorogenic or chemiluminogenic substrates with different emission characteristics are used. For fluorescence, an exemplary examples is the use of fluorescein and an anti-fluorescein-galactose conjugate. The time dependence or signal strength of the fluorescence or chemiluminescence signal and the emission wavelength can also additionally be used for decoding.

Alternatively, the cleavable primer and/or the noncleavable primer are modified with varying numbers Iso-G and Iso-C (which are orthogonal to standard base pairs). Biotin- and/or Dig labeled iso-G and iso-C are then incorporated during the amplification reaction and are finally detected by a reaction cascade as mentioned above. Orthogonal flaps which are capable for specific interaction with a counterpart but could not interact with DNA or RNA attached to the 5' end of the primers could also be used for "decoding by hybridization" on an array where the counterparts of the flaps are immobilized on a specific known position. Suitable orthogonal flaps are nucleic acid analogs like isoG iso C containing oligo-nucleotides, L-DNA, GNA and homoDNA.

Many other different encoding strategies are known in literature and some of them are commercially available. Examples are disclosed in the following references:
  Fluorescence: Tong, A. K. et al., Nature Biotechnology 19 (2001) 756-759
  Mass: Kokoris, M. et al., Molecular Diagnosis 5 (2000) 329-340
  Raman spectroscopy: Sun, L. et al., Analytical Chemistry 79 (2007) 3981-3988, Ng, P., Nucleic Acids Research 34 (2006) e84/1-e84/10
  Reviews on multiplex analysis: Finkel, N. H. et al., Anal. Chem. 76 (2004) 352A-359A, Braeckmans, K. et al., Nat. Rev. Drug Discov. 1 (2002) 447-456

In a particular embodiment, encoded beads can also be used in combination with the detection modes of using either fluorescent entities like dsDNA binding dyes or fluorescent hybridization probes as disclosed above.

(iii) Real Time PCR

In case clonal isolation of step c) has been achieved by means of distribution of said plurality of beads into the cavities of a micro- or picotiter plate, the PCR reaction of step can already be monitored in real time during step e) as disclosed above using an appropriate detection format. In other words, steps e) and f) are performed simultaneously by means of performing Real Time PCR analysis.

Many different beads, each containing primer pairs for different genes are pooled. The target is hybridized to the beads. A micro device such as a picotiter plate (PTP) is used for physically separating different beads each carrying two PCR primers both specific for one gene. One of the primers immobilized on the beads contains a cleavable linker. PCR reagents are added to the beads physically separated on the PTP. The beads are then exposed to cleavage conditions to cut the linker attaching the cleavable primer to the support matrix. The reaction mixture is exposed to PCR cycling. The still immobilized (non-cleavable) primer hybridizes to amplified molecules in close proximity—holding them at the surface. PCR is performed within the single wells of the PTP and been followed in real time. Also in this embodiment, the amplicons may subsequently be subjected to a thermal gradient in order to perform a melting curve analysis.

In order to identify the amplification products in Real Time it is recognized by a person skilled in the art that same modes of encoding the beads may be applied. It is also recognized by a person skilled in the art that for detection of amplification product, double stranded DNA binding dyes or fluorescent hybridization probes as disclosed above for end point PCR analysis can be used.

Moreover, it is possible to use any kind of detection format which is known in the art of real time PCR. In particular, it is also possible to use he well known TaqMan 5' nuclease for-mat. In this case, a single-stranded Hybridization Probe is labeled with two components. When the first component is excited with light of a suitable wavelength, the absorbed energy is transferred to the second component, the so-called quencher, according to the principle of fluorescence resonance energy transfer. During the annealing step of the PCR reaction, the hybridization probe binds to the target DNA and is degraded by the 5'-3' exonuclease activity of the Taq Polymerase during the subsequent elongation phase. As a result the excited fluorescent component and the quencher are spatially separated from one another and thus a fluorescence emission of the first component can be measured (U.S. Pat. No. 5,804,375). However, this assay format is incompatible with a subsequent melting curve analysis.

(iv) Library Preparation

In addition to methods of analyzing multiple nucleic acid molecules directly, the present invention further provides for a library made by the methods of the invention. The library may be made by using, e.g., genomic DNA, total cellular cDNA, a genomic DNA library, a cDNA library, or a plasmid library as the starting material for amplification. The library may be derived from any population of nucleic acids, e.g., biological or synthetic in origin.

Thus, more precisely, the present invention is also directed to a method for the amplification of multiple nucleic acid molecules of interest comprising in the steps of
  a) providing a plurality of beads, characterized in that each bead comprises at least one pair of sequence specific amplification primers, further characterized in that at least one of said primers is bound to the bead via a cleavable linker,
  b) capturing the nucleic acid molecules of interest from a sample,
  c) clonally isolating said plurality of beads,
  d) cleaving said at least one primer,
  e) clonally amplifying said nucleic acid thereby creating multiple amplification products, and
  f) storing said multiple amplification products clonally in the cavities of a micro- or picotiter plate.

In case step c) is done by means of preparing an emulsion according to the present invention, then step f) comprises in the beginning the step of distributing said plurality of beads into the cavities of a micro- or picotiter plate. In case step c) comprises the step of distributing said plurality of beads into the cavities of a micro- or picotiter plate, the amplification products may be stored directly within the same micro- or picotiter plate.

In case previously prepared libraries are amplified according to the invention, then it is possible to use one type of bead with one specific pair of amplification primers. In case genomic DNA or total cellular cDNA is amplified according to the invention, the beads must comprise a population of randomized forward and reverse primer sequences.

In addition, the, the present invention is also directed to a library prepared by the methods disclosed above.

Applications of the Invention (i) Sequencing

The sequencing analysis according to the present invention can be used for a variety of different applications In many cases it is desired to analyze multiple copies of a particular target for potential sequence variations. According to the present invention, the pre-amplification of a certain target by PCR which is necessary according to methods known in the art is avoided. Instead, according to the present invention, the emPCR itself is performed with multiple beads of the same type, characterized in that all beads are carrying the same pair of amplification primers.

Thus, in one aspect, the sequencing analysis according to the present invention may be used for quantitative mutational analysis. In this aspect, the data obtained from the plurality of different sequencing reactions reveal a plurality of different variations which occur in the target nucleic acid from a sample that has been amplified. In addition, the obtained data provide quantitative information, on the percentage, how frequently each sequence variation was originally present in the analyzed sample.

Moreover, such an analysis can also be done in a multiplex approach. In this case, the sequence variations of several different target nucleic acids which are present in a sample are determined. The number of different targets that can be analyzed by this method is only limited by the number of different beads that can be provided in such a way that each bead carries a specific pair of amplification primers.

In another aspect, it is also possible to analyze a complex gene or a gene locus, the sequence of which cannot be amplified be means of performing only a single PCR reaction. In this case, multiple different species of beads are provided, characterized in that each bead carries a specific pair of amplification primers designed to amplify a particular region of the target DNA that shall become analyzed. In this context, the design of the primers must be done in such a way that the sizes of the generated amplification products do not exceed a length, which cannot become completely sequenced in the subsequent sequencing step. Thus, preferably, the generated amplicon sizes are below 1000 and most preferably below 500 nucleotides. Also preferably, the sequences of the generated amplicons comprise overlaps between each other so that the finally generated sequence information comprises a high degree of confidence without any gaps.

In particular, such an analysis is useful in order to analyze multiple polymorphisms found in particular genes or gene loci, which have been proven to be associated with a predisposition of a certain disease or for the prognosis of a disease. For example, the inventive method can be used to analyze human genes such as the gene encoding muscular dystrophy or the HNPCC genes.

In a further aspect, the sequencing analysis according to the present invention may be used for monitoring gene expression. In this aspect, cDNA is used which has been prepared in such a way that the 5' end has a target sequence which is capable of acting as a primer binding side for the subsequent amplification reaction. As a second primer within said amplification reaction, an oligo-dT primer may be used. Introduction of the primer binding side at the 5' end of the cDNA may be performed by any method known in the art. For example, for second strand cDNA synthesis, it is possible to use a primer comprising a 5' part and a 3' part. The 5' part comprises the primer binding side which by itself does not hybridize to the first strand cDNA. The 3' part comprises an at least partially and preferably completely randomized sequence such that is capable of hybridizing to substantially all first strand cDNA molecules.

Alternatively, if only expression of a limited number of target nucleic acids shall be amplified, first strand and second cDNA synthesis are performed with a population comprising a limited number of primer sequences. For first strand cDNA synthesis, a composition of primers is used which share a first common 5' part corresponding to a first amplification primer binding side, but corresponding to the different number of targets that shall be monitored all have different 3' parts. Similarly, for second strand cDNA synthesis, a composition of primers is used which share a second common 5' part corresponding to a first amplification primer binding side, but corresponding to the different number of targets that shall be monitored all have different 3' ends.

Similar to the quantitative mutational analysis method, the data obtained by subsequent sequencing also reveal quantitative information on how often which cDNAs are represented within the original sample.

In a further side aspect, the pair of sequence specific amplification primers may be replaced by a population of completely randomized primers. If this is the case, the method according to the present invention may also be used to sequence a population of nucleic acid molecules with many different sequences such as a sample of genomic DNA or a sample of total cDNA.

(ii) End Point PCR and Real Time PCR

The PCR embodiments according to the present invention can be used for absolute or relative nucleic acid quantification.

In case of relative quantification, at least two pairs of sequence specific amplification primers are used in order to amplify two different nucleic acid sequences which are present in a sample. The photo cleavable primers preferably comprise different tags for subsequent detection, i.e. Each member of the plurality of primers which are bound to the bead via a cleavable linker carries a different detectable label. Alternatively, if only a limited number of targets shall be analyzed. The amplification products are discriminated by means of melting curve analysis, by means of using differentially labeled hybridization probes or by means using Digoxygenin or Biotin encoded primers. The sample may be for example a genomic DNA sample, a cDNA sample or an RNA sample. In the latter case, a one-step RT-PCR has to perform.

In case of absolute quantification, the sample is spiked with a known amount of standard nucleic acid, which may be amplified with primers as disclosed above and detected by means of either appropriately tagged primers or appropriately labeled probes.

In case of end point PCR monitoring, the abundance of positive signals for each type of amplified target sequence is determined and compared to each other in order to obtain relative or (—in case of usage of a known standard—) absolute quantification data.

In case of real time PCR, quantitative data are obtained during the amplification process according to protocols well known and frequently used in the art.

Thus, with both end point PCR monitoring and real time PCR monitoring according to the invention it is possible to compare the abundance of different RNAs in an original sample, or in other words, it is possible to monitor gene expression in a relative manner.

In a further aspect, the present ends point PCR as well as real time PCR methods may be used for mutational analysis according the protocols based on the allele specific amplification, which is also called ARMS technology (U.S. Pat. Nos. 5,137,806, 5,595,890, 5,639,611). In this particular embodiment, primers with 3' discriminating nucleotide residue are use, which are capable of amplifying only one particular sequence variation of a particular target sequence, but do not amplify a second known sequence variation.

EXAMPLES

Example 1

Preparation of Primers and Photocleavable Primers

Oligonucleotide synthesis was carried out on a 4 times 1 µmol scale on an ABI 394 synthesizer. Commercially available tac CPG (Proligo) was used as the support material. All other chemicals for the standard synthesis were obtained from Glen Research. Phosphoramidites with tert butylphenoxy-acetyl protective groups (known as "tac" or "Expedite" monomers) from Proligo were used. As capping reagent tertbutylphenoxyacetyl acetic anhydride (tac2O) in tetrahydrofuran was used.

The following commercially available modifiers were used:

5' Amino modifier C6: (6-(4-Monomethoxytritylamino) hexyl-(2-cyanoethyl)-(N,N-diisopropyl)-phosphoramidite Spacer phosphoramidite 18 (18-O-Dimethoxytritylhexaethyleneglycol, 1-[(2-cyanoethyl)-(N,N-diisopropyl)]-phosphoramidite Photocleavble spacer [4-(4,4'-Dimethoxytrityloxy)butyramidomethyl)-1-(2-nitrophenyl)-ethyl]-2-cyanoethyl-(N,N-diisopropyl)-phosphoramidite BiotindT phosphoramidite (5'-Dimethoxytrityloxy-5-[N-((4-t-butylbenzoyl)-biotinyl)-aminohexyl)-3-acrylimido]-2'-deoxyUridine-3'-[(2-cyanoethyl)-(N,N-diisopropyl)]-phosphoramidite)

Biotin phosphroamidite (1-Dimethoxytrityloxy-2-(N-biotinyl-4-aminobutyl)-propyl-3-O-(2-cyanoethyl)-(N, N-diisopropyl)-phosphoramidite)

Fluorescien phosphoramidite (1-Dimethoxytrityloxy-2-(N-thiourea-(di-O-pivaloyl-fluorescein)-4-aminobutyl)-propyl-3-O-(2-cyanoethyl)-(N,N-diisopropyl)-phosphoramidite)

Fluorescein dT phosphoramidite (5'-Dimethoxytrityloxy-5-[N-((3',6'-dipivaloylfluoresceinyl)-aminohexyl)-3-acrylimido]-2'-deoxyUridine-3'-[(2-cyanoethyl)-(N,N-diisopropyl)]-phosphoramidite)

The standard protocol was used for the synthesis. The product was cleaved from the support for 2 h at room temperature with 33% ammonia and purified by reversed phase chromatography on a Porous Oligo R34.6×50 mm column. Chromatography: buffer A: 0.1 M triethylammonium acetate in water pH 6.8, buffer B: 0.1 M triethylammonium acetate in water/acetonitrile 1:1, gradient 2 min 0% B to 100% B in 45 min. The UV absorption of the eluant was measured at 260 nm. A main fraction was obtained which contained the aminomodified oligonucleotide. The solvent was removed on a vacuum centrifuge.

The following table shows sequences and modifications of oligonucleotide primer immobilized to N-hydroxysuccinimide ester (NHS)-activated Sepharose beads. Capital letters represent generic adaptor sequences for bead encoding, amplification, enrichment and pyrosequencing, whilst lower case letters represent gene specific sequences.

TABLE 2

| Sequence-ID | Target gene | Sequence (5'->3') |
|---|---|---|
| #1 | — | 5'-AmMC6-(isp18)$_3$-PCL-C-$^{FAM}$dT-GTGCGTCCCTACTCTACC (SEQ ID NO: 1) |
| #2 | — | 5'-AmMC6-(isp18)$_3$-CCTATCCCTGT GTGCCTTG (SEQ ID NO: 2) |
| #3 | — | 5'-AmMC6-(isp18)$_3$-PCL-T$^B$-CCATCTCATCCCTGCGTGTC (SEQ ID NO: 3) |

TABLE 2-continued

| Sequence-ID | Target gene | Sequence (5'->3') |
|---|---|---|
| #4 | NM_004048 (B2M) | 5'-AmMC6-(isp18)$_3$-GCCTCCCTCGCGCCATCAG<u>cctgg</u> tctttctatctcttgtactac (SEQ ID NO: 4) |
| #5 | NM_004048 (B2M) | 5'-AmMC6-(isp18)$_3$-PCL-T$^B$-GCCTTGCCAGCCCGCTCAGgcatcttcaa acctccatga (SEQ ID NO: 5) |
| #6 | NM_199166 (ALAS) | 5'-AmMC6-(isp18)$_3$-GCCTCCCTCGCGCCATCAG<u>cctgg</u> aatgagtcgccacccacg (SEQ ID NO: 6) |
| #7 | NM_199166 (ALAS) | 5'-AmMC6-(isp18)$_3$-PCL-T$^B$-GCCTTGCCAGCCCGCTCAGagctcccgc tctaagtcca (SEQ ID NO: 7) |
| #8 | NM_000194 (HPRT) | 5'-AmMC6-(isp18)$_3$-GCCTCCCTCGCGCCATCAG<u>cctggactgta</u> gattttatcagactga (SEQ ID NO: 8) |
| #9 | NM_000194 (HPRT) | 5'-AmMC6-(isp18)$_3$-PCL-T$^B$-GCCTTGCCAGCCCGCTCAGtggattat actgcctgaccaa (SEQ ID NO: 9) |
| #10 | NM_000190 (PBGD) | 5'-AmMC6-(isp18)$_3$-GCCTCCCTCGCGCCATCAGgcggagcca tgtctggtaa (SEQ ID NO: 10) |
| #11 | NM_000190 (PBGD) | 5'-AmMC6-(isp18)$_3$-PCL-T$^B$-GCCTTGCCAGCCCGCTCAGccagggtac gaggctttcaa (SEQ ID NO: 11) |

5'-AmMC6 . . . 5'-amino-modifier C6
isp18 . . . internal spacer 18, hexa-ethylene glycol
PCL . . . photo-cleavable 2-Nitrobenzyl linker
FAMdT . . . Fluorescein deoxy-thymidine
TB = Biotin deoxy-thymidine
Mval restriction site is underlined Example 2

Preparation of Beads and Photocleavage

Figure 2:
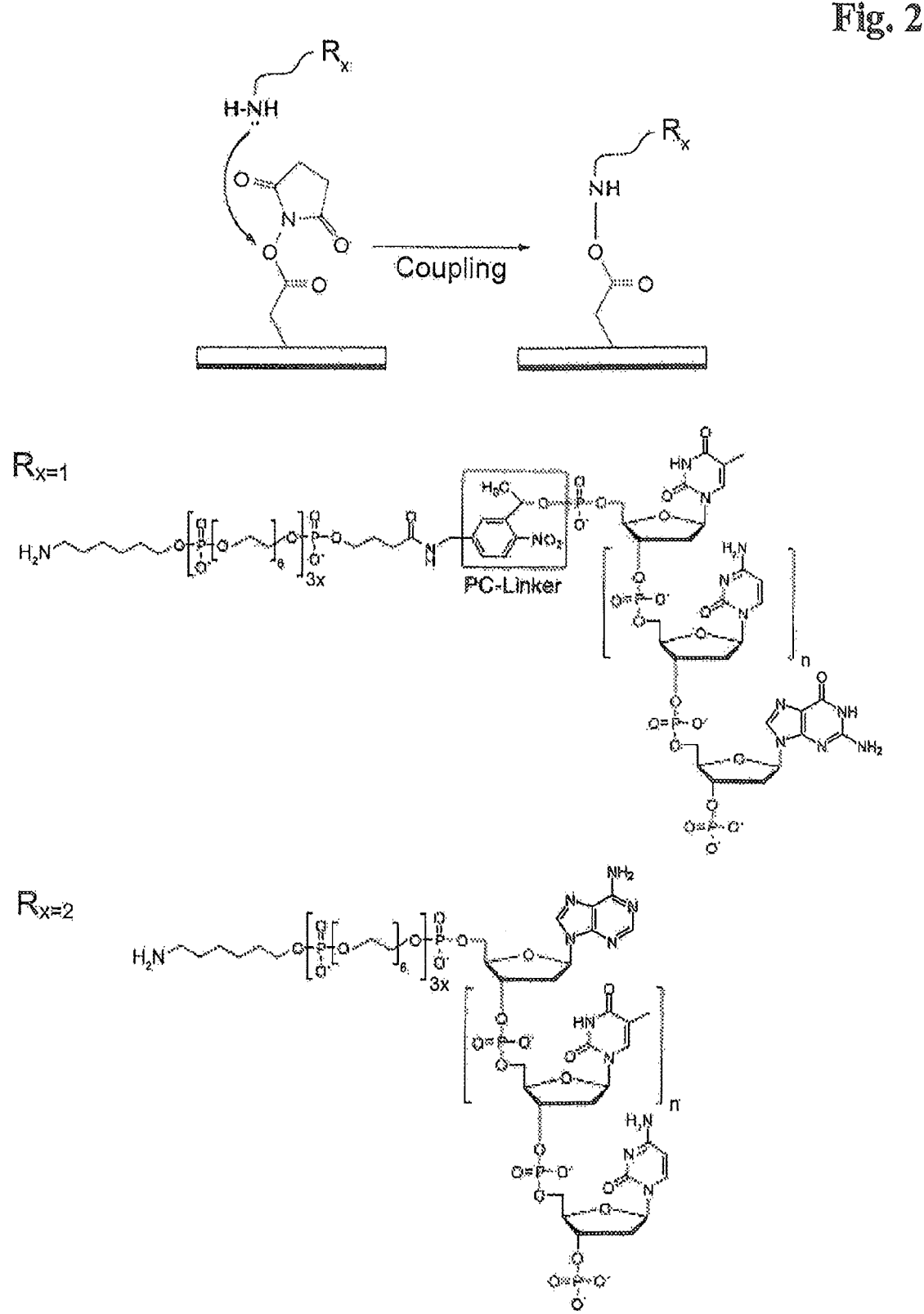
FIG. 2 illustrates the N-hydroxysuccinimide ester (NHS) conjugation chemistry, whereas Rx=1 represents a photo-cleavable primer and Rx=2 a stationary primer.

Amino-modified oligonucleotides containing stationary and photo-cleavable linker (sequence-ID #1-9) respectively, were conjugated to N-hydroxysuccinimide ester (NHS) functionalized sepharose beads (Roche/454-Life Sciences, Branford, Conn., USA) according to the standard protocol. The chemical reaction mechanism is represented in FIG. 2.

To trigger photocleavage of the Nitrobenzyl linker these beads were subjected to UV irradiation in a QS1.000 quartz cell (1-cm path length) using a 8 W dual wavelength UV lamp (Camag, Berlin, Germany) at 366 nm. The distance between quartz cell and UV lamp was 2 cm.

Example 3

Analysis of the Photocleavage Reaction
(Corresponding to FIG. 3)

This example describes the detection of the photocleavage of fluorescein-modified oligonucleotide probes immobilized to sepharose beads.

5×10$^6$ of beads conjugated with fluorescein-modified oligonucleotide probes (sequence-ID #1) were extensively washed, then suspended in 100 µl 50 mM Tris/HCl pH 7.5 buffer and irradiated for 15 min as described in example 2. Subsequently the beads were centrifuged and the supernatant was analyzed for photocleaved fluorescein-modified oligonucleotides (FAM) by absorbance measurement using a NanoDrop 1000 spectrophotometer (Thermo Scientific, Waltham, Mass., USA) (FIG. 3A).

In addition, 0.6×106 beads carrying fluorescein-modified oligonucleotide probes (sequence-ID #1) were suspended in 800 µl PCR-reaction mixture (Table 3).

TABLE 3

| Reagent | final concentration |
| --- | --- |
| Tween-80 | 0.01% |
| BSA | 0.10% |
| $MgSO_4$ | 2.5 mM |
| Glycerol | 3.6% |
| $Tris-H_2SO_4$ pH 8.9 | 58.1 mM |
| $NH_4-SO_4$ | 17.4 mM |
| dATP, dGTP, dCTP, dTTP | each 0.40 mM |
| Expand HiFi-Taq polymerase | 0.04 U/µl |

Alternatively, the same amount of beads was suspended in 190 µl PCR-reaction mixture that was in turn emulsified according to manufacturer's instructions (GS emPCR kit User's Manual, Roche/454-Life Sciences, Branford, Conn., USA). Suspended or emulsified beads were irradiated for 15 min as described in example 2. Thereafter beads were extensively washed with isopropanol and 50 mM Tris/HCl pH 7.5 buffer. Photo-cleavage was analyzed by measuring the fluorescence intensity of beads before and after irradiation using a standard flow cytometer (FIG. 3B). As it can be deduced from the figure, photocleavage by means of UV irradiation in both cases resulted in a significant loss of fluorescence intensity of the bead population.

Example 4

Photo-Activated Bead PCR (Corresponding to FIGS. 4 and 5)

This example describes the detection of specific PCR products using bead PCR and photo-cleavable bead immobilized primer. Template for bead PCR and a standard control PCR was an artificial 239 by amplicon. The amplicon was designed in such a way that it contains a Mva I and a Nla III restriction site. Restriction endonuclease treatment of this amplicon after bead PCR or the control PCR is expected to result in characteristic patterns of different length fragments as predicted in FIG. 4.

0.3×106 beads carrying stationary and photo-cleavable oligonucleotide probes (sequence-ID #2, #3) were suspended in 100 µl PCR-reaction mixture (Table 3) containing 1 pg of an artificial 239 by amplicon. The amplicon included a sequence that was complementary to the oligonucleotides on the beads. The suspension was irradiated for 15 min as described in example 2. Thereafter the suspension was transferred into PCR reaction chambers (i.e. PCR tubes). PCR was performed in a standard thermocycler as follows:

1 cycle (4 minutes at 94° C.)—hotstart initiation 40 cycles (30 seconds at 94° C., 60 seconds at 58° C., 90 seconds at 68° C.)—denaturing, annealing, polymerization 25 cycles (30 seconds at 94° C., 6 minutes at 58° C.)—denaturing, polymerization;

Storage at 10° C.

After completion of the PCR reaction, the beads carrying the amplified material were removed, washed in 50 mM Tris/HCl pH 7.5 buffer and subjected to restriction endonuclease treatment (ca. 5 U) for 2 h at 37° C. Subsequently beads were centrifuged and the supernatant was analyzed for specific PCR products by agarose gel electrophoresis (FIG. 5 right side). A control PCR reaction was performed using non-immobilized oligonucleotide probes (FIG. 5, left side). As can be seen in FIG. 5, the bead PCR resulted in the expected large and small DNA fragments, indicating that photo-cleavage and bead PCR reaction have both worked successfully.

Example 5

Photo-Activated Bead Emulsion-PCR (Corresponding to FIG. 6)

This example describes the detection of specific PCR products using bead emulsion PCR and photocleavable bead immobilized primer.

0.4×106 beads carrying stationary and photo-cleavable oligonucleotide probes (sequence-ID #2, #3) were suspended in 30 µl Capture Buffer (2 mM Tris/HCl pH 7.5, 0.5 mM Mg(CH3-COO)2) containing 4 pg of an artificial 239 by amplicon. The amplicon included a sequence that was complementary to the oligonucleotides on the beads. The amplicon was hybridized to the beads in a standard thermocycler as follows:

1 cycle (5 minutes at 80° C.)—denaturing;

1 cycle (decrease 0.1° C./second to 70° C., 1 minutes at 70° C.)—annealing;

1 cycle (decrease 0.1° C./second to 60° C., 1 minutes at 60° C.)—annealing;

1 cycle (decrease 0.1° C./second to 50° C., 1 minutes at 50° C.)—annealing;

1 cycle (decrease 0.1° C./second to 20° C., 5 minutes at 20° C.)—annealing.

Subsequently the beads were emulsified according to manufacturer's instructions (GS emPCR kit User's Manual, Roche/454-Life Sciences, Branford, Conn., USA). The emulsion was irradiated for 30 min as described in example 2. Thereafter the emulsion was transferred into PCR reaction chambers (i.e. PCR tubes). PCR was performed in a standard thermocycler as follows:

1 cycle (4 minutes at 94° C.)—hotstart initiation;

40 cycles (30 seconds at 94° C., 60 seconds at 58° C., 90 seconds at 68° C.)—denaturing, annealing, polymerization;

25 cycles (30 seconds at 94° C., 6 minutes at 58° C.)—denaturing, polymerization;

Storage at 10° C.

After completion of the PCR reaction, the emulsified beads were recovered by a series of wash and centrifugations steps using first an excess of isopropanol, second an excess of ethanol buffer (10 mM Tris/HCl pH 7.5, 70% ethanol) and third 50 mM Tris/HCl pH 7.5 buffer. The washed beads were then subjected to restriction endonuclease treatment (ca. 5 U) for 2 h at 37° C. Subsequently beads were centrifuged and the supernatant was analyzed for specific PCR products by agarose gel electrophoresis. As control a PCR reaction was performed using non-immobilized oligonucleotide probes. As it is shown in FIG. 6, the bead emulsion PCR and subsequent restriction endonuclease treatment resulted in the generation of the expected DNA fragment, indicating that photo-cleavage and subsequent emPCR reaction have both worked successfully.

Example 6

Photo-Activated Bead Emulsion-PCR Using cDNA as Template (Corresponding to FIG. 7)

This example describes the detection of specific PCR products from human cDNA using bead emulsion PCR and photocleavable bead immobilized primer.

$0.4 \times 10^6$ beads carrying stationary and photo-cleavable oligonucleotide probes specific for the Beta-2 microglobulin gene (sequence-ID #4, #5) were suspended in 30 µl Capture Buffer (2 mM Tris/HCl pH 7.5, 0.5 mM Mg(CH3-COO)2) containing human cDNA obtained from the HeLa cell line.

The cDNA was incubated with the beads using the hybridization procedure of example 5. Subsequently the beads were emulsified, irradiated and subjected to amplification by PCR as outlined in example 5.

After completion of the PCR reaction, the emulsified beads were recovered as described in example 5. The washed beads were then subjected to restriction endonuclease treatment and analyzed for specific PCR products by agarose gel electrophoresis. As control photo-activated bead emulsion-PCR was performed using 2.4 pg of a 147 by amplicon of the Beta-2 microglobulin gene as template. The expected DNA fragment as shown in FIG. 7 indicates that photo-cleavage and subsequent emPCR reaction have both worked successfully with human cDNA as template. Similar results have been obtained using HeLa cDNA and beads carrying stationary and photo-cleavable oligonucleotide probes specific for the prophobilinogen deaminase gene (sequence-ID #10, #11).

Example 7

Multiplexed Photo-Activated Bead-PCR (Corresponding to FIGS. 8 and 9)

The following procedures, including capture of multiple template DNAs, DNA amplification, and recovery of a set of distinct beads bound to their corresponding amplified template, were performed in a single tube.

a) Multiplexed Photo-Activated Bead-PCR in Suspension

This example describes the simultaneous detection of multiple, specific PCR products using photo-activated bead PCR in suspension (FIG. 8).

A set of distinct beads ($0.2 \times 10^6$ beads each) covalently attached to stationary and photo-cleavable oligonucleotide probes specific for the genes aminolaevulinate synthase, beta-2 microglobulin and hypoxanthine-guanine phosphoribosyltransferase (sequence-ID #4, #5, #6, #7, #8, #9) was suspended in 100 µl PCR-reaction mixture (Table 3). This suspension was supplemented with amplicons (ca. 0.5 pg each) of the genes aminolaevulinate synthase (127 bp), beta-2 microglobulin (174 bp) and hypoxanthine-guanine phosphoribosyltransferase (181 bp). The suspension was irradiated and subjected to amplification by PCR as outlined in example 4.

After completion of the PCR reaction, the beads were washed and subjected to restriction endonuclease treatment as described in example 4. After centrifugation of the beads the supernatant was analyzed for specific PCR products using a microfluidic, chromatographic chip (2100 Bioanlyzer, Agilent Technologies, Santa Clara, Calif., USA).

Results are shown in FIG. 9 a. Clearly, 3 different peaks were obtained, which represent fragment sizes that correspond to the fragment sizes which are theoretically expected for 127 bp, 174 by and 181 by amplicons.

b) Multiplexed Photo-Activated Bead-PCR in Emulsion

This example describes the simultaneous detection of multiple, specific PCR products using photo-activated bead PCR in emulsion (FIG. 8).

A set of distinct beads ($0.2 \times 10^6$ beads each) covalently attached to stationary and photo-cleavable oligonucleotide probes specific for the genes aminolaevulinate synthase, beta-2 microglobulin and hypoxanthine-guanine phosphoribosyltransferase (sequence-ID #4, #5, #6, #7, #8, #9) was suspended in 30 µl Capture Buffer (2 mM Tris/HCl pH 7.5, 0.5 mM Mg(CH$_3$—COO)$_2$). The Capture buffer contained amplicons (ca. 1.5 pg each) of the genes aminolaevulinate synthase (127 bp), beta-2 microglobulin (174 bp) and hypoxanthine-guanine phosphoribosyltransferase (181 bp).

The DNA was hybridized to the beads according to the procedure of example 5. Subsequently the beads were emulsified, irradiated and subjected to amplification by PCR as outlined in example 5. After completion of the PCR reaction, the emulsified beads were recovered as described in example 5. The washed beads were then subjected to restriction endonuclease treatment (ca. 5 U) for 2 h at 37° C. After centrifugation of the beads the supernatant was analyzed for specific PCR products (FIG. 9B) using a microfluidic, chromatographic chip (2100 Bioanlyzer, Agilent Technologies, Santa Clara, Calif., USA).

Results are shown in FIG. 9 b. Again, 3 different peaks were obtained, which represent fragment sizes that correspond to the fragment sizes which are theoretically expected for 127 bp, 174 by and 181 by amplicons. Thus the results clearly demonstrate that the present invention is highly valuable for multiplex applications in solution as well as in the form of emulsion PCR.

Example 8

Nucleic Acid Sequencing Using Singleplex Photo-Activated Bead Emulsion PCR

The following experiment was performed to test the specific detection of a target sequence obtained after bead emulsion PCR using a high throughput sequencing system based on pyrophosphate sequencing (Margulies, M., et al., Nature 437 (2005) 376-80).

For this protocol $0.4 \times 10^6$ sepharose beads, with an average diameter of 25-35 µm, were covalently attached to stationary and photo-cleavable oligonucleotide probes (sequence-ID #2, #3). These beads were mixed with 4 pg of an artificial 239 by amplicon. The amplicon included a sequence that was complementary to the oligonucleotides on the beads.

The amplicon was annealed to the beads, emulsified, irradiated and amplified by PCR using the procedure in example 5. After completion of the PCR reaction, the emulsified beads were recovered as described in example 5. The DNA on the washed beads was rendered single stranded and sequencing primer was annealed according to manufacturer's instructions (GS emPCR kit User's Manual, Roche/454-Life Sciences, Branford, Conn., USA). Next, 250 000 beads were sequenced simultaneously by pyrophosphate sequencing using the Genome Sequencer FLX from Roche/454-Life Sciences (Branford, Conn., USA). Data processing using the software GS Amplicon Variant Analyzer confirmed the exclusive detection of the indicated amplicon.

Example 9

Nucleic Acid Sequencing Using Multiplex Photo-Activated Bead Emulsion PCR

The following experiment was performed to test the simultaneous detection and decoding of target sequences obtained after multiplexed bead emulsion PCR using a high throughput sequencing system based on pyrophosphate sequencing (Margulies, M., et al., Nature 437 (2005) 376-80).

For this protocol a set of distinct beads, with an average diameter of 25-35 μm, was used whereas each bead type was covalently attached to stationary and photo-cleavable oligonucleotide probes specific for the genes aminolaevulinate synthase, beta-2 microglobulin and hypoxanthine-guanine phosphoribosyltransferase (sequence-ID #4, #5, #6, #7, #8, #9). $0.6 \times 10^6$ beads at $0.2 \times 10^6$ beads for each bead type were mixed with amplicons (ca. 0.5 pg each) of the genes aminolaevulinate synthase (127 bp), beta-2 microglobulin (174 bp) and hypoxanthine-guanine phosphoribosyltransferase (181 bp). The amplicons were annealed to the beads, emulsified, irradiated and amplified by PCR using the procedure in example 5. After completion of the PCR reaction, the emulsified beads were recovered as described in example 5.

The DNA on the washed beads was rendered single stranded and sequencing primer was annealed according to manufacturer's instructions (GS emPCR kit User's Manual, Roche/454-Life Sciences, Branford, Conn., USA). Next, 250 000 beads were sequenced simultaneously by pyrophosphate sequencing using the Genome Sequencer FLX from Roche/454-Life Sciences (Branford, Conn., USA). Data processing using the software GS Amplicon Variant Analyzer confirmed the simultaneous detection of a mixture of different amplicons.

What is claimed is:

1. An emulsion comprising two or more types of micelle, each micelle comprising:

a bead, said bead comprising at least one pair of sequence specific amplification primers specific for a target nucleic acid wherein the at least one pair includes a first primer and a second primer, said first primer comprising a first nucleotide sequence and said second primer comprising a second nucleotide sequence different from the first nucleotide sequence, said first primer bound to said bead with an inducible photo-cleavable linker via a functional moiety selected from the group consisting of carboxy, aldehyde, azide, alkyne, amino, thiol, sulfonylalken, iodoacetyl, amino hydrazine, hydroxylamino, and maleimido, and said second primer is covalently attached to the bead via a second linker different from the inducible photo-cleavable linker of the first primer and is not cleavable under cleavage conditions for the first primer, and wherein the at least one pair of sequence specific amplification primers in each of the two or more types of micelle is specific for a different target nucleic acid.

2. The emulsion of claim 1, wherein said bead is comprised of a material selected from the group consisting of silicon, titanium dioxide, aluminum oxide, lanthanide oxide, glass, silicates polystyrene, cellulose, Sepharose, and polyamide.

3. The emulsion of claim 1, wherein the first primer carries a detectable tag.

4. The emulsion of claim 1, wherein said bead has a size between about 10 μm to about 250 μm.

* * * * *

```
                              SEQUENCE LISTING

<160> NUMBER OF SEQ ID NOS: 11

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tgtgcgtccc tactctacc                                                    19

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cctatcccct gtgtgccttg                                                   20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ccatctcatc cctgcgtgtc                                                   20

<210> SEQ ID NO 4
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gcctccctcg cgccatcagc ctggtctttc tatctcttgt actac                       45

<210> SEQ ID NO 5
<211> LENGTH: 39
<212> TYPE: DNA
<213> ORGANISM: Artificial Sequence
<220> FEATURE:
<223> OTHER INFORMATION: Description of Artificial Sequence: Synthetic
```

-continued primer

<400> SEQUENCE: 5
gccttgccag cccgctcagg catcttcaaa cctccatga         39

<210> SEQ ID NO 6
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gcctccctcg cgccatcagc ctggaatgag tcgccaccca cg         42

<210> SEQ ID NO 7
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gccttgccag cccgctcagc agctcccgct ctaagtcca         39

<210> SEQ ID NO 8
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gcctccctcg cgccatcagc ctggactgta gattttatca gactga         46

<210> SEQ ID NO 9
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gccttgccag cccgctcagt ggattatact gcctgaccaa         40

<210> SEQ ID NO 10
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gcctccctcg cgccatcagg cggagccatg tctggtaa         38

```
<210> SEQ ID NO 11
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gccttgccag cccgctcagc cagggtacga ggctttcaa                              39
```